United States Patent
Ahlquist et al.

(10) Patent No.: US 7,563,597 B2
(45) Date of Patent: Jul. 21, 2009

(54) PRODUCTION OF PACKAGED DNA SEQUENCES

(75) Inventors: Paul G. Ahlquist, Madison, WI (US); Dohun Pyeon, Madison, WI (US); Paul F. Lambert, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 318 days.

(21) Appl. No.: 11/275,819

(22) Filed: Jan. 30, 2006

(65) Prior Publication Data

US 2009/0148950 A1    Jun. 11, 2009

Related U.S. Application Data

(60) Provisional application No. 60/648,539, filed on Jan. 31, 2005.

(51) Int. Cl.
*C12P 21/00*    (2006.01)

(52) U.S. Cl. .................... 435/69.1; 435/71.1; 435/320.1

(58) Field of Classification Search ........................ None
See application file for complete search history.

(56) References Cited

OTHER PUBLICATIONS

Buck C, et al., "Efficient intracellular assembly of papillomaviral vectors," J. Virol. 78:751-757 (2004).
Holmgren S, et al., "The minor capsid protein L2 contributes to two steps in the human papillomavirus type 31 life cycle," J. Virol. 79:3938-3948 (2005).
Buck, Christopher B, et al., "Efficient intracellular assembly of papillomaviral vectors", J of Virology, v. 78, No. 2, Jan. 2004, pp. 751-757.
Pastrana, D V, et al., "Reactivity of human sera in a sensitive, high-throughput pseudovirus-based . . .", Virology, v. 321, No. 2, Apr. 10, 2004, pp. 205-216.
Stauffer, Y, et al., "Infectious human papillomavirus type 18 pseudovirions", J of Molecular Biology, v. 283, No. 3, Oct. 30, 1998, pp. 529-536.
Pyeon, Dohun, et al. "Production of infectious human papillomavirus . . .", Proceedings Nat'l Acad of Sciences of the USA, v. 102, No. 26, Jun. 2005, pp. 9311-9316.

*Primary Examiner*—Stacy B Chen
(74) *Attorney, Agent, or Firm*—Quarles & Brady LLP

(57) ABSTRACT

A method of producing a packaged DNA sequence is disclosed. In one embodiment, the method comprises the steps of: (a) selecting a DNA sequence to be packaged and a papillomaviral capsid sequence, wherein the DNA sequence to be packaged is between 7 Kb-8.5 Kb, (b) co-transfecting the products of step (a) into transfectable cells, wherein the DNA sequence is packaged, and (c) purifying packaged particles.

8 Claims, 10 Drawing Sheets

A

B

C

D

E

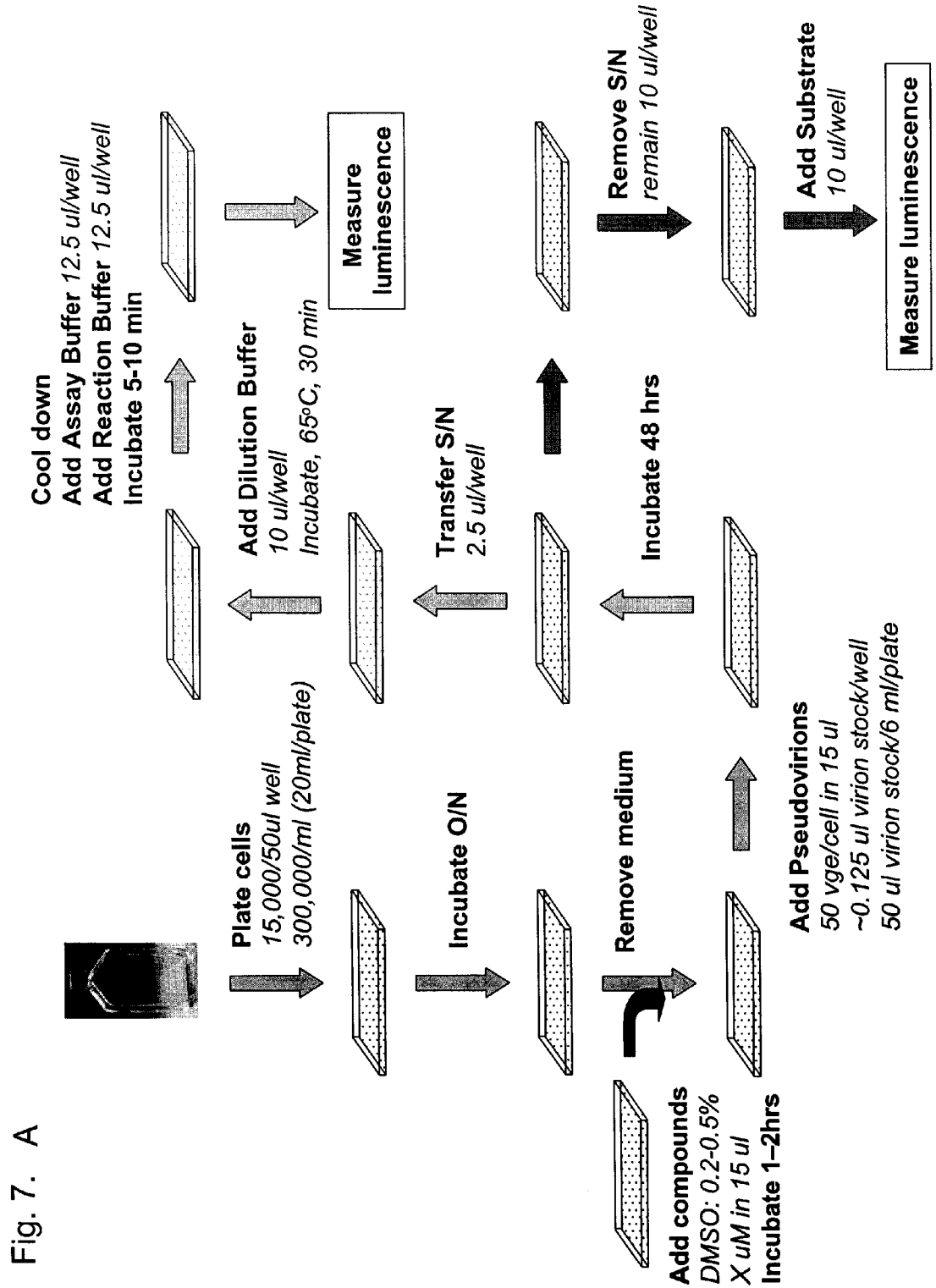
Fig. 7. A

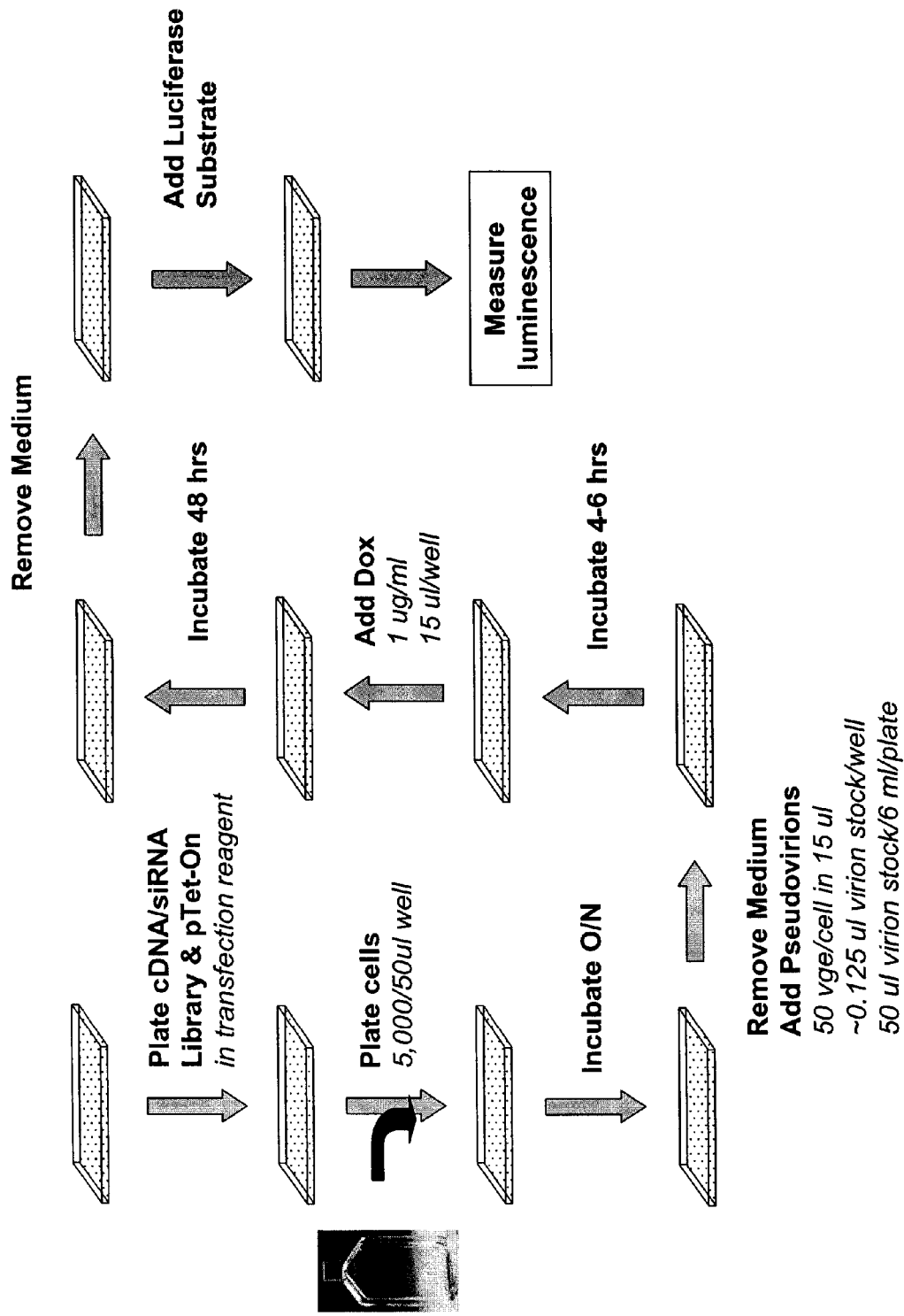
Fig. 7. B

US 7,563,597 B2

PRODUCTION OF PACKAGED DNA SEQUENCES

CROSS-REFERENCES TO RELATED APPLICATION

This application claims priority to U.S. provisional application 60/648,539, filed Jan. 31, 2005, incorporated by reference as if fully set forth herein.

STATEMENT REGARDING FEDERALLY SPONSORED RESEARCH OR DEVELOPMENT

This invention was made with United States government support awarded by the following agencies:
NIH CA022443
The United States government has certain rights in this invention.

BACKGROUND OF THE INVENTION

The present invention relates to the creation of DNA sequences coated with papillomavirus capsid proteins L1 and L2. In particular, the present invention relates to the packaging of papillomaviral genomic DNAs and thereby the efficient generation of infectious papillomavirus particles containing wild type or modified viral genomic DNAs.

Papillomaviruses are non-enveloped, double-stranded DNA viruses with ~8 kb, circular genomes, 55 nm spherical capsid coats, wide distribution in higher vertebrates and tight species specificity. Human papillomaviruses (HPVs), of which there are over 100 genotypes, infect and replicate in cutaneous or mucosal epithelia, inducing benign lesions including warts that are self-limiting and normally regress over time. A subset of the mucosotropic HPVs (HPV), termed the high risk genotypes such as HPV16, 18, and 31, are causally associated with anogenital cancers, including nearly if not all cervical carcinoma, a leading cause of death by cancer among women worldwide. In addition high risk HPVs, in particular HPV16, are associated with 20-30% of head and neck cancers, though here an etiological role has yet to be clearly established.

The HPV life cycle is tightly linked to epithelial differentiation. HPVs initially infect cells of the poorly differentiated, proliferative, basal compartment of stratified epithelia. Here the viral genome sets up residence as a low copy nuclear plasmid and a subset of viral genes, termed the early genes are expressed at low levels. No progeny virus is made in basal cells. However, as infected basal cells grow and divide and daughter cells migrate into the suprabasal compartment to undergo terminal differentiation, the productive stage of the viral life cycle is initiated. Here the virus reprograms suprabasal cells to support the amplification of the viral genome to high copy number, the viral structural genes encoding the major and minor capsid proteins, L1 and L2, respectively are expressed, progeny virions are assembled and these virions then are released into the environment from the most superficial layers of the epithelia. The requirement for terminal differentiation of epithelial cells to support the productive stage of the viral life cycle precludes obtaining infectious virus particles from conventional cell culture. Consequently, the only prior methods capable of producing infectious papillomavirus virions were organotypic culture, a process by which small quantities of artificial skin can be produced in cell culture, or alternatively the use of xenografts in immunodeficient mice. However, these methods are technically demanding, time-consuming, variable, produce only relatively low virus yields, and require access to epithelial cell populations or human tissue in which the viral genotype of interest persists as a nuclear plasmid. These limitations have severely restricted the availability of infectious human as well as some animal papillomaviruses for basic, preclinical and clinical research.

Recently, Buck and Schiller developed a new approach to papillomavirus packaging in which reporter plasmids were encapsidated into bovine papillomaviral capsid proteins expressed in transiently transfected mammalian cells (J. Virol. 78:751-757, 2004). High levels of papillomavirus L1 and L2 capsid proteins were expressed from codon-optimized synthetic genes in 293TT human embryonic kidney cells, which stably express SV40 large T antigen to enhance replication of SV40 origin-containing plasmids. When cotransfected into 293TT cells with L1- and L2-expression plasmids, target plasmids of less than 6 kb were efficiently encapsidated into the resulting papillomavirus capsids. This method allowed for the differentiation-independent generation of virus-like transducing particles. However, Buck, et al. concluded that intracellular packaging of target plasmids into these papillomavirus-like transducing particles by this approach was limited by a strong size discrimination to target plasmids of 6 kb or less, far under the natural viral genome size of approximately 8 kb.

What remained in need is a method that permits for the efficient encapsidation of full-length and near-full length papillomaviral genomes into the papillomaviral capsids. This would allow for the efficient generation of infectious papillomavirus particles.

BRIEF SUMMARY OF THE INVENTION

In one embodiment, the present invention is a method of producing a packaged DNA sequence comprising the steps of: (a) selecting a DNA sequence to be packaged and a papillomavirus capsid sequence, wherein the packaged sequence is between 7 Kb-8.5 Kb, (b) co-transfecting the products of step (a) into transfectable cells, and (c) purifying virus particles, wherein the virus particles preferably comprise at least 50 protected DNA copies per cell. Preferably, the packaged DNA sequence is a papillomaviral DNA genome and preferably the product of the method is an infectious virion. In another embodiment, a native or wild type papillomaviral DNA genome is modified before packaging or a wild type HPV capsid sequence is modified before packaging.

In a preferred form of the present invention, the DNA sequence to be packaged is previously cloned into a plasmid, amplified in a suitable host, isolated and recircularized, and the HPV capsid sequence is modified by optimizing the codons and cloning the sequence into an expression plasmid.

In another embodiment, the present invention is the packaged product of the method described above. Other embodiments, advantages and functions of the present invention will be apparent to one of skill in the art upon review of the specification, claims and drawings.

BRIEF DESCRIPTION OF THE SEVERAL VIEWS OF THE DRAWINGS

FIG. 7 is an illustration of a preferred high throughput screening procedure. FIG. 7A illustrates exposure of HPV particles to small molecule compounds. FIG. 7B illustrates exposure of HPV particles to cDNA and siRNA.

DETAILED DESCRIPTION OF THE INVENTION

1. In General

Figure 1:
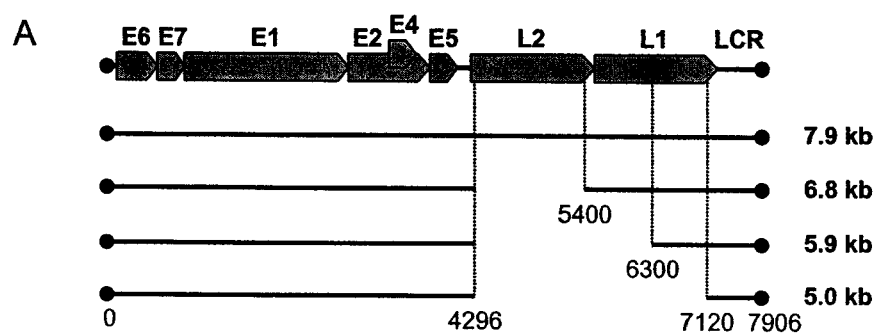
FIG. 1. Encapsidation of HPV16 genome and its derivatives by HPV16 L1 and L2 capsid proteins. Different sizes of HPV16 genome derivatives were generated by PCR at the HPV16 genome position shown by the numbers (A). Each target DNA was co-transfected into 293TT cells with HPV16 L1 and L2 expressing plasmid. Following Optiprep gradient purification of the virus particles, encapsidated DNA was analyzed on 0.8% agarose gel electrophoresis and SYBR green staining (B-D), and HPV16 L1 capsid proteins were visualized by western blotting with mouse anti-HPV16 L1 antibody (CAMVIR) (C). The full length HPV16 genome-encapsidated virus particles indicated by the arrow were used for following infection assays (C). A reporter plasmid, pSEAP-control (Clontech), was transfected alone or co-transfected with both HPV16 L1 and L2, or only HPV16 L1 expressing plasmids, and virus particles were purified by Optiprep gradient (D).
Figure 1:
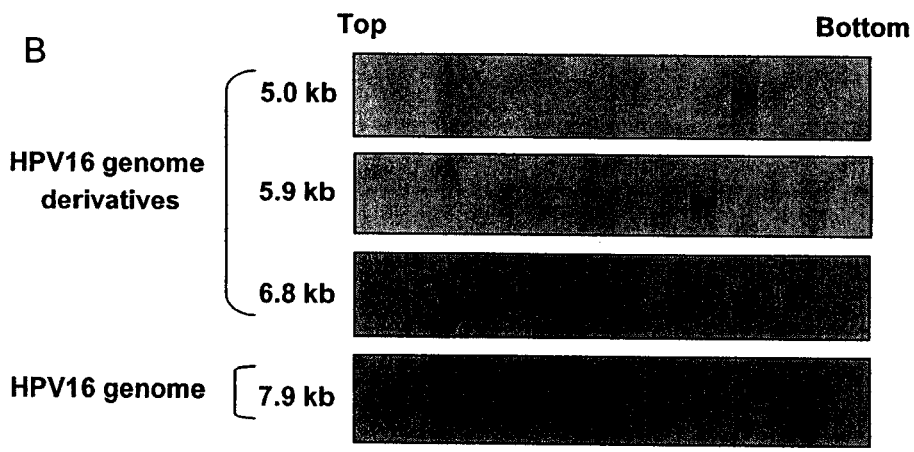
Figure 1:
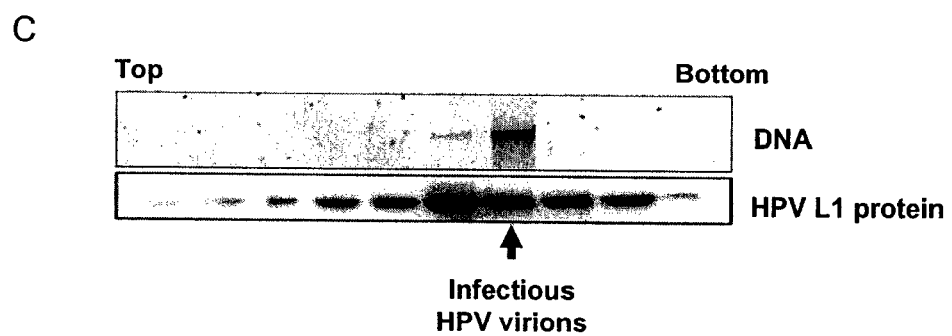
Figure 1:
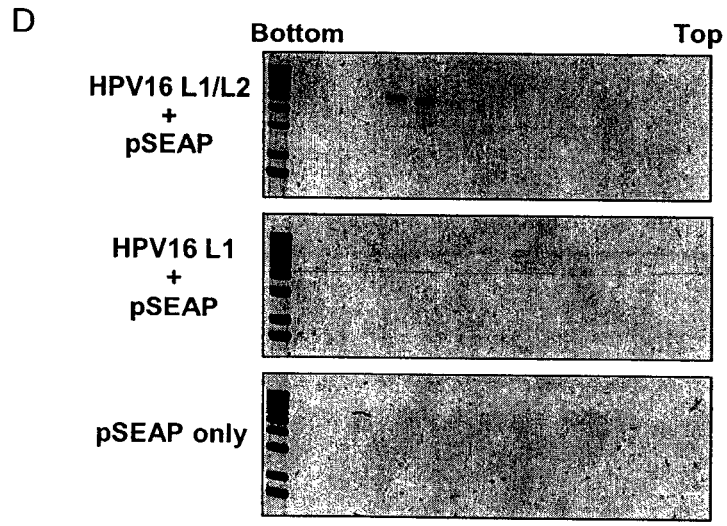

Papillomaviruses are small DNA virus associated with benign and malignant epithelial lesions including >95% of cervical cancers and ~20% of head and neck cancers. Because papillomavirus replication and virion production are tied to epithelial cell differentiation, infectious papillomavirus virion production has been limited to cumbersome organotypic cultures and mouse xenografts. Consequent difficulties in obtaining useful amounts of wild-type or mutant HPV virions have greatly limited studies on many aspects of papillomavirus biology.

To overcome these limitations, we have developed an efficient system to encapsidate DNA sequences, such as the full-length papillomaviral genome, into packaged (preferably infectious) virus particles, independently of viral DNA replication and epithelial differentiation. By "encapsidated" or "packaged" we mean that a DNA sequence of over 7 Kb is contained within HPV capsid proteins, L1 and L2. Preferably, this packaged DNA sequence is obtained from a papillomaviral DNA genome or an altered or deleted form of a papillomaviral DNA genome. Preferably, the packaged DNA sequence is a full-length or near full-length (at least 95%) papillomaviral sequence and the resulting particle is an infectious virion.

This transient, transfection-based system can produce over 1000 times more infectious virus than the much more labor-intensive organotypic culture. Furthermore, this method allows for the facile generation of infectious and non-infectious particles containing wild-type, mutant, or chimeric papillomaviral genomes and overcomes barriers to studies of many facets of replication, host interactions, vaccine and drug development previously limited by insufficient availability of infectious virions.

2. Production of Infectious Human Papillomavirus

In one embodiment, the present invention includes the production of packaged human papillomavirus, preferably infectious virus. The chart below describes a generalized way of performing one typical embodiment of the present invention.

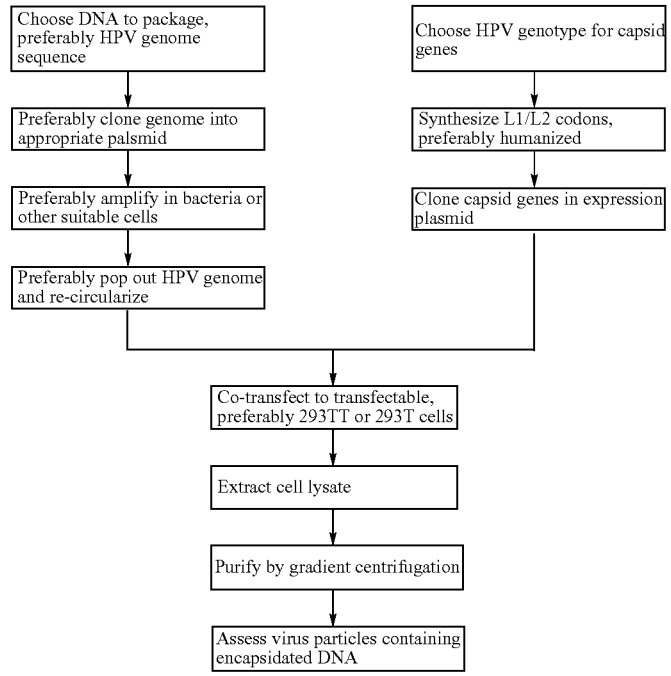

In general, one would first choose a DNA sequence, preferably an HPV genotype that one wished to package. In one embodiment of the invention, this HPV genotype is any of the known HPV genotypes and comprises a genome of approximately 8 kb (±10%). Most preferably, we envision that the following HPV genotypes would be most useful for the present invention: HPV genotypes 16, 18, 31, 6, 11, 32, 33, 38, 45, 58, 5, 8, 12, 13, 17, 22, 30, 34, 35, 39, 42, 43, 44, 51, 52, 53, 54, 55, 56, 57, 59, 61, 66, 67, 68, 69, 70, 72 and 83. In one preferred version of the present invention, one would package genotypes 16, 18, 6, 11 or 31. See list of references at end of specification for citations. In another embodiment, the papillomaviral genomic sequence comprises an animal papillomavirus sequence, for example canine oral papillomavirus, rhesus papillomavirus type 1, cottontail rabbit papillomavirus, and rabbit oral papillomavirus.

By "segment of an HPV genome" we mean that one of skill would take segments of a native HPV genome to package. These segments may not comprise the entire native HPV genome. For example, our examples below demonstrate that the entire HPV genome isn't necessary for early viral gene transcription. Example III demonstrates that one may remove the HPV16 L1 and L2 open reading frame sequences. Therefore, one may wish to combine an HPV genotype with deleted L1 and L2 sequences (either partially or entirely deleted) combined with non-native HPV sequences to create a nucleic acid sequence between 7 and 8.5 Kb. We mean for the phrase "segment of an HPV genome" to include this truncated HPV genome and any other segment of a native HPV genome combined with non-native sequences.

The example below demonstrates efficacy of the present invention with HPV16 and HPV31. We envision that other HPV strains will be suitable because:

1. All known HPV genotypes have genomes of very similar size (~8 kb) and almost identical capsid structures (Lowy, D. R. and P. M. Howley, Papillomaviruses. Fields Virology. D. M. Knipe and P. M. Howley. Philadelphia, Lippincott-Raven Publishers. 2:2231-2264, 2001).
2. In all known HPV strains, expression of L1/L2 or L1 alone assemble HPV virion-like particles (VLPs) (Zhou, et al., *Virology* 185(1):251-257, 1991; Kirnbauer, et al., *J. Virol.* 67(12):6929-6936, 1993; Volpers, et al., *Virology* 200(2):504-512, 1994; Unckell, et al., *J. Virol.* 71(4):2934-2939, 1997).
3. As shown in Holmgren, et al., *J. Virol* 79(7) 3938-3948, 2005, and other references, L2 is critical for efficient packaging of DNA in HPV capsid structure and for viral infectivity (Zhou, et al., *J. Virol.* 68(2):619-625, 1994; Okun, et al., *J. Virol.* 75(9):4332-4342, 2001; Exhibit A).
4. Infectious virus particles were successfully produced from organotypic raft culture with numerous species including HPV16 (McLaughlin-Drubin, et al., *Virology.* 322(2):213-219, 2004), HPV18 (Meyers, et al., *J. Virol.* 71(10):7381-7386, 1997), HPV16/18 chimera (Meyers, et al., *J. Virol.* 76(10):4723-4733, 2002), HPV31 (Meyers, et al., *Science.* 257(5072):971-973, 1992), HPV45 (McLaughlin-Drubin, et al., *Virology.* 312(1):1-7, 2003), HPV11 (Christensen, et al., *J. Gen. Virol.* 75 (Pt 9):2271-2276, 1994), and BPV-1, wherein for the latter, cultures were grafted on mice (McBride, et al., *Proc. Natl. Acad. Sci. USA.* 97(10):5534-5539, 2000).

As described below in "Other Embodiments", in one embodiment the present invention is designed to package modified viral genomes. For example, these modifications may be substitutions, additions and deletions. The method of the present invention is suitable for packaging viral genomes or DNA sequences between 7 Kb through 8.5 Kb.

One would typically clone the selected HPV genome into an appropriate plasmid. We have chosen to use pRL-null (Promega) However, only a small fragment (~2 kb) that contains bacterial origin (f1) and ampicillin resistance gene are used. Those genes are included in most bacterial cloning vectors. Full-length HPV genome was previously cloned into pUC19. Thus, the general requirements for this plasmid vehicle are existence of i) a bacterial origin for DNA amplification in E. coli and ii) a selection marker for appropriate selection of plasmid-containing clones from unwanted bacteria.

One may wish to skip these steps of cloning and amplifying the HPV genome. One may wish to simply combine linear DNA fragments of interest with the L1 and L2 packaging proteins, similar to the method of long PCR. For example, packaged DNA could also be prepared without bacterial cloning steps, using alternative DNA preparations such as high fidelity long PCR. See Cline J, Braman J C, Hogrefe H H. PCR fidelity of pfu DNA polymerase and other thermostable DNA polymerases. *Nucleic Acids Res.* 1996 Sep. 15; 24(18): 3546-51 and Gao F. Amplification and cloning of near full-length HIV-2 genomes. *Methods Mol Biol.* 2005; 304:399-407.

The HPV genome construct we used in the Examples contained some bacterial sequences of ampicillin-resistant genes and f1 bacterial origin used to amplify the DNA in bacterial culture. However, before transfection into 293TT cells, these non-HPV DNA sequences are preferably removed and only HPV genome sequence is introduced into 293TT cells.

One would then amplify the plasmid in a suitable host cell and isolate the HPV genome. Preferably, one would recircularize the HPV genome and cotransfect with capsid genes into suitable transfectable cells, such as 293TT cells.

Simultaneously with the HPV genome cloning, one would typically choose an HPV genotype for capsid genes. It is not necessary that the HPV genotype selected for capsid genes be of the same strain as the HPV genotype selected for packaging. As discussed above, we envision that the present invention would be useful for any HPV genotypes because of the high degree of similarity in the capsid genes.

In the Examples, HPV genomes were packaged in VLPs generated by expression L1 and L2 from a single plasmid. However, other alternative expression approaches, well known to those skilled in the art, could readily be used. For example, one might express L1 and L2 from a separate plasmid, e.g. pcDNA3.1(+)-HPV16L1 and pcDNA3.1(+)-HPV16L2 (Leder, et al., *J. Virol.* 75:9201-9202, 2001). However, VLPs generated by expressing HPV16L1 alone (i.e. in the absence of L2) did not package target DNAs to detectable levels, consistent with prior studies demonstrating a requirement for L2 for efficient DNA encapsidation (Roden, et al., *J. Virol.* 70:5875-5883, 1996; Holmgren, et al., *J. Virol. In press*, 2005).

One would preferably synthesize an optimized (or "humanized") sequence by reference to the following references: Zhou, J., et al., *J. Virol.* 73(6):4972-4982, 1999; Leder, C., et al. *J. Virol.* 75(19): 9201-9209, 2001. The optimized sequences would typically be cloned into an expression plasmid and co-transfected, as described above, into 293TT cells. The Examples below describes one typical method of co-transfection.

One would then extract the cell lysate and purify the virus particles containing encapsidated DNA, typically as described in the Examples.

293TT cells are a daughter cell line of human embryonic kidney cell line 293T for additional SV40 T antigen overexpression. We envision that other cell lines could substitute for the 293TT cells mentioned in the Examples and above. We refer to these suitable cells as "transfectable cells" because it is important that the cell line be highly transfectable. 293TT cells stably overexpress additional SV40 large T antigen cDNA. We have done this transfection in 293T cells, a parental cell line of 293TT expressing less large T antigen, and did not see any major difference. However, the suitable cell line does not have to stably overexpress additional SV40 large T antigen. SV40 large T antigen is useful for target DNA replication so that one may simply add more DNA in transfection to overcome shortage of DNA.

We envision that epithelial cell lines such as HeLa, RKO, and Ca Ski be suitable. For example, one may wish to use a cell line other than the 293T or 293TT cell line if one uses a different amplification system that does not depend on the amplification of the SV40 T antigen. High L1/L2 capsid protein expression is essential for this packaging method. However, even though SV40 T antigen expressing cell lines maintain high copy number of transfected L1/L2 plasmid and express high amount of protein, other cell lines lacking SV40 T antigen such as HeLa, CHO, and CaSki are also efficiently express a large amount of proteins from transfected DNA. Thus, this packaging method would be used with a variety of different cell lines that show high transfection efficiency combined with high protein expression, not exclusive to 293T and 293TT cells. In addition, another element Epstein Barr Virus (EBV) ori P could be used to maintain high copy number of transfected plasmid. See Hung, S. C., Kang, M. S., and Kieff, E. (2001). *Proc. Natl. Acad. Sci. USA* 98, 1865-1870.

The method of the present invention typically results in at least 50 packaged or protected DNA copies per cell, preferably 100, more preferably 200, and most preferably at least 250 copies per cell.

| | Encapsidated DNA Yield | | | |
|---|---|---|---|---|
| | Buck and Schiller (J. Virol. 78:751, 2004) | | | HPV16 genome (8 kb) |
| | 6 kb plasmid with SV40 ori[a] | 6 kb plasmid without SV40 ori[a] | 8 kb plasmid without SV40 ori[b] | (the present) invention, results from embodiment in Examples) |
| No. of L1 VLP equivalents/cell | 52,000 | 37,000 | ~37,000 | ~36,000 |
| No. of protected DNA copies/cell | 600 | 100 | ~7 | ~250 |

Figure 2:
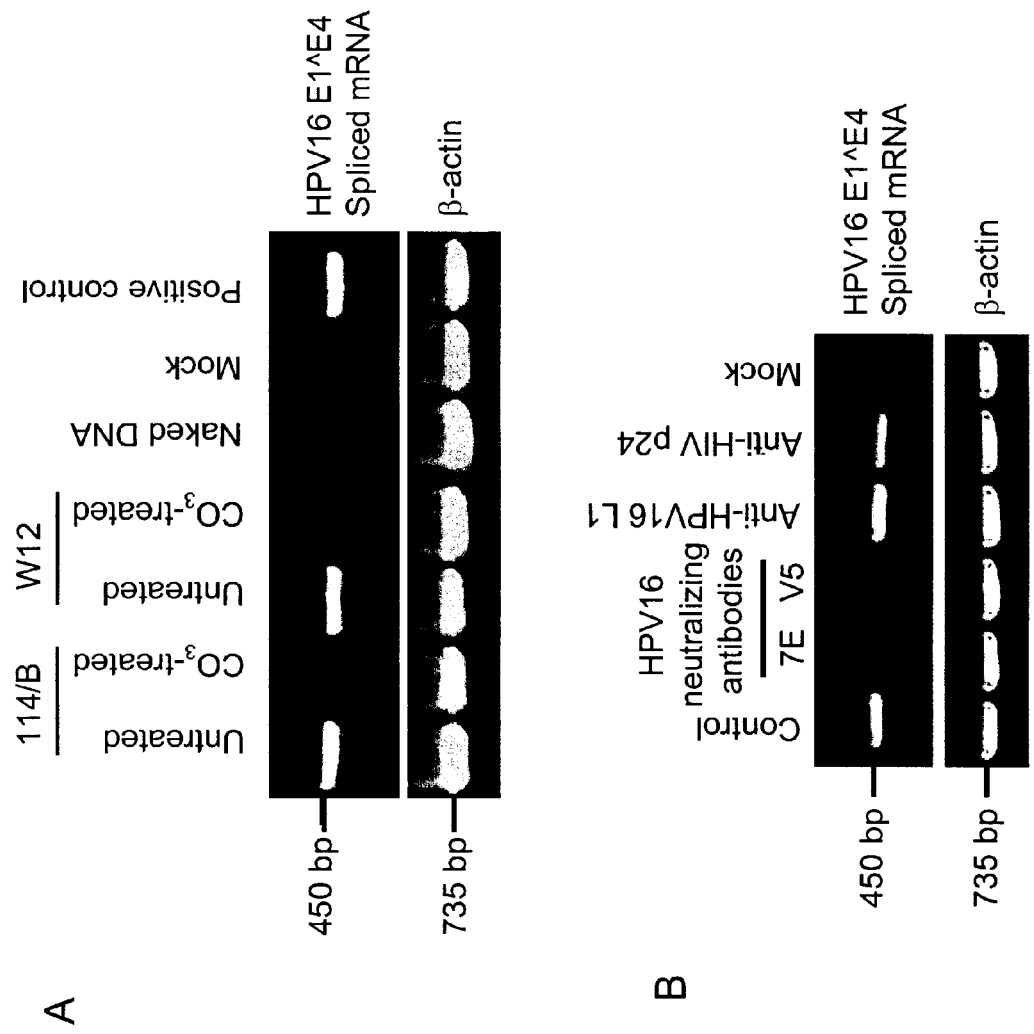
FIG. 2. Infectivity of full length HPV16 encapsidated virions packaged in 293TT cells. Virions encapsidated with HPV16 114B or W12 genome was inoculated into HaCaT cells following the treatment with or without high pH carbonate buffer for 24 hours at 4° C. (A). After two day incubation, cells were harvested, total RNA was isolated, and nested RT-PCR was performed with the PCR primers (Table 1) to detect E1^E4 spliced mRNA. Total RNA extracted from W12 cells was used as a positive control and b-actin mRNA was amplified simultaneously as standards. Recircularized HPV16 114B DNA was added directly into HaCaT cells as another control. HPV16 L1 neutralizing antibodies, H16.7E and H16.V5, were incubated with 293TT cell-packaged HPV16 at 1:100 dilutions for 1 hour at 4° C., before infection (B). Other isotype antibodies, non-neutralizing anti-HPV16 L1 antibody and anti-HIV Gag, were used as negative controls.

[a]From Table 1.
[b]Derived from Table 1 and ratio of GFP-expressing cells between 6 kb and 8 kb plasmids (FIG. 2)

In the Example below, our transfection-based system was more efficient for HPV genomes than previous organotypic culture methods. The table above compares the method of the present invention with Buck and Schiller, J. Virol. 78:751, 2004. Note that the method presented in Buck and Schiller was able to produce only approximately seven protected DNA copies per cell in an attempt to package an 8 kb plasmid. The method of the present invention resulted in packaging of 250 copies, a 35-fold increase.

We envision that one may wish to create packaged viral particles or may wish to create infectious virus particles. If one wishes to create infectious virus particles, the Example below discloses one typical method for checking and evaluating infectivity.

OTHER EMBODIMENTS

The following are additional embodiments of the present invention.

Vaccine Development and testing for neutralizing antibodies: The efficacy of prophylactic vaccines relates to the induction of neutralizing antibodies. Screening for such antibodies requires the availability of infectious virus. The present invention allows for the production of infectious HPVs for any desired HPV genotype.

High throughput screening for therapeutic targets and drug candidates: The virus quantity produced by the present invention would be sufficient for large scale high throughput screenings of siRNA and small molecule libraries. Most preferably, a highput screening method would be as follows:

The general concept of these assay systems would be applied to screen modulators of any infection stages of all HPV genotypes, including 16, 18, 31, 6, 11, 32, 33, 38, 45, 58, 5, 8, 12, 13, 17, 22, 30, 34, 35, 39, 42, 43, 44, 51, 52, 53, 54, 55, 56, 57, 59, 61, 66, 67, 68, 69, 70, 72 and 83. For example, the modulators may either block or enhance infection. Candidate modulators would be initially screened from any of publicly and commercially available chemical compound libraries and cDNA, siRNA, and shRNA expression libraries. Depending on necessity, the assay system would be modified using other applicable promoters and reporters inserted or replaced in any region of HPV genome.

FIGS. 7 A and B illustrates particularly advantageous embodiments. Referring to FIG. 7, for small molecule screening, 10,000 cells per well are plated in 384-well plates and incubated overnight at 37° C. On the next day, small molecule compounds are added to each well one hour prior to adding the virus particles of the present invention containing SV40 promoter driven SEAP (50 vge/well). After 48 hour incubation at 37° C., 2.5 µl of culture supernatant is transferred to a new 384-well plate for SEAP assay, while remaining cells are used for cell cytotoxicity assay using Cell-Titer Glo Cell Viability Assay kit from Promega (FIG. 7A). SEAP activity indicates successful HPV entry and gene expression in host cells. Compounds that are a "hit" will decrease SEAP activity.

For cDNA and siRNA screening, pTet-On plasmid and cDNA or siRNA from libraries are combined with transfection reagent (Mirus Transit) and distributed in 384-well plates. 5,000 cells per well are then added to each well for reverse transfection, incubating overnight at 37° C. Next day, after removing culture medium, 50 vge/cell of chimeric HPV containing TRE driven RL in late region of HPV16 genome is added to each well and cells are incubated at 37° C. for 4 to 6 hours. Reporter gene expression is induced with 1 µg/ml doxycycline. After 48 hour induction, culture medium is removed and luciferase substrate in cell lysis buffer is directly added to the cells (FIG. 7B). RL activity indicates successful HPV entry and gene expression in host cells. "Hit" compounds will decrease RL activity. In addition, this assay system would be very useful for secondary screening of small molecule hits and initially screened cDNA and siRNA, with which any possible effect of HPV early genes and long control region (LCR) can be easily assayed.

Generation of infectious animal papillomavirus: Parts or all of animal papillomaviral genomic sequences (unmodified or modified to include mutations in viral sequences or to contain nonviral DNA sequences) could be packaged in capsids formed with their own capsid proteins or the capsid proteins of other papillomaviruses thereby producing infectious virus particles for basic and preclinical research. Examples of preferred animal papillomaviruses are canine oral papillomavirus, rhesus papillomavirus type 1, cottontail rabbit papillomavirus, and rabbit oral papillomavirus.

Application for gene therapy using HPV derived vectors: Parts of the HPV genomic DNA could be replaced to deliver and express desired foreign gene(s).

Development of therapeutic/prophylactic vaccines against HPV or other agents: Since it is easy to assemble a defective genome into original capsid proteins, developing live attenuated viruses would be possible to trigger cell-mediated immune response.

Identifying natural HPV receptor(s) on host cells

Genetic engineering of designed HPV mutant derivatives for research, virus attenuation, vaccine, gene therapy or other uses

EXAMPLES

I. Production of Infectious Human Papillomavirus Independently of Viral Replication and Epithelial Cell Differentiation In this report, we describe the extension of the transient transfection method to achieve the successful and efficient packaging of the full length HPV genomes into HPV16 capsids. We demonstrate that the resulting HPV virions are highly infectious in their natural, host epithelial cells. Importantly, a single 10 cm dish of 293TT cells, following a simple two-day transient transfection, yielded more than a 1000 times greater amount of infectious virus that obtained from the much more labor-intensive and time-consuming organotypic culture. By providing a ready, manipulatable source of infectious papillomavirus virions, these approaches open up many studies of HPV replication, vaccine and drug development previously limited or blocked by the difficulty of producing infectious HPV virions.

Materials and Methods

Plasmids. Recombinant clones of full-length HPVs, pEF399, containing the W12 HPV16 genome, pBSHPV16 (114/B), containing the 114B genome, pBSHPV16(114/K) containing the 114K genome, pHPV31b, containing the HPV31b genomes were previously described (Flores, et al., 1999; Mueller and Gissman—for 114B and 114K; Laimins for HPV31b). The plasmid, pXULL, expressing both codon optimized HPV16 L1 and L2, as well as those expressing codon optimized HPV16 L1 and L2 individually (pcDNA-HPV16L1 and pcDNA-HPV16L2) was obtained from John Schiller. The pSEAP-control vector was purchased from Clontech. Recombinant plasmids containing subgenomic fragments of the HPV16 W12E genome, of 5.0 kb, 5.9 kb, and 6.8 kb in length, were generated by cloning PCR amplified segments of the viral genome into XhoI- and SacI-cleaved pRL-null (Promega). The 5.0, 5.9 and 6.8 kb HPV subgenome fragments, deleted for nts 4296-7120, 4296-6300 and 4296-5400 of the viral genome, respectively, were generated by PCR using pfu DNA polymerase along with the sense primer, TTATAAAGTTGGGTAGCCGATGCACG (SEQ. ID NO: 1) and an anti-sense primer, TCTACAACTGCTAAACG-CAAAAAA (5.0 kb) (SEQ. ID NO: 2), CTGGATATTTGTA-CATCTATTTGC (5.9 kb) (SEQ. ID NO: 3), or TCTTTAT-CAGGTTATATTCC (6.8 kb) (SEQ. ID NO: 4). PCR was performed for 32 cycles consisting of 1 minute at 94° C. for denaturation, 1 minute at 58° C. for annealing, and 14 minutes at 72° C. for polymerization, followed by 20 minutes at 72° C. for extension. For transfection into 293TT cells, the full length of subgenomic HPV DNAs were released from the bacterial vector by restriction enzyme digestion (BamHI for full length HPV16 and HPV31b genomes, XhoI for subgenomic HPV16 clones), and re-circularized by ligation under conditions that favor monomeric ligation events as previously described (Genther, et al., 2003).

Cell lines. Human embryonic kidney cell line 293T, purchased from ATCC, and its SV40 T antigen-expressing daughter cell line 293TT (Buck, C. B., et al., *J. Virol* 78(2): 751-757, 2004), acquired from John Schiller, were maintained in Dulbecco's modified eagle's medium (DMEM) (Invitrogen) supplemented with 10% fetal bovine serum (FBS) (Invitrogen). Immortalized human keratinocyte cell line HaCaT (Boukamp, P., et al., *J. Cell Biol.* 106(3):761-771, 1988) was maintained in F-media (Invitrogen, 3 parts of F-12 and 1 part of DMEM), supplemented with 10% FBS. W12E cells, clone 20850 (Jeon, et al., 1995), harboring extrachromosomal HPV16 genomes were maintained on mitomycin C (4 µg/ml, Sigma)-treated 3T3 mouse fibroblast in F-media supplemented with 0.4 µg of hydrocortisone (Calbiochem), 0.1 nM of cholera toxin (ICN), 5 µg/ml of insulin (Sigma), 25 µg/ml of adenine (Sigma), 10 ng/ml of epidermal growth factor (R&D Systems), and 5% FBS as previously described (Jeon, et al., 1995).

Virus packaging and purification. 293TT cells, plated in a 10 cm dish one day before, were co-transfected with HPV16 capsid protein expression plasmids as indicated, and one of the target DNAs for encapsidation, such as the full length HPV16 genome or the pSEAP-control plasmid, using Lipofectamine2000 (Invitrogen). After 48 hours at 37° C., the cells were harvested and resuspended in phosphate-buffered saline (PBS) with 9.5 mM $MgCl_2$. The cells were lysed by adding Brij58 to a final concentration of 0.25%, followed by addition of 0.3% benzonase (Sigma) and 2 U/100 µl of exonuclease V (Epicenter) and incubation at 37° C. for 24 hours to remove unpackaged free cellular and viral DNA and to allow capsid maturation. The lysate was incubated on ice for 10 minutes with addition of 0.17 volumes of 5 M NaCl and centrifuged at 2000×g for 10 minutes at 4° C. The resulting cleared supernatant was loaded on top of a 27-33-39% Optiprep/PBS-0.8M NaCl density gradient and centrifuged in an SW60 rotor at 234,000×g for 4 hours at 16° C. Two hundred µl fractions of the centrifuged lysate were collected by bottom puncturing the bottom of the tube. Aliquots of 10 µl from each fraction were analyzed by 10% sodium dodecyl sulfate polyacrylamide gel electrophoresis (SDS-PAGE) and western blotting. Briefly, proteins fractionated by SDS-PAGE were transferred on polyvinylidene difluoride (PVDF) paper (Amersham). HPV16 L1 protein bands were visualized by chemiluminescence using a mouse anti-HPV16 L1 antibody, CAMVIR-1 (Abcam), and goat anti-mouse IgG conjugated with horse radish peroxidase (Jackson ImmunoResearch). To assay for DNA encapsidation, DNA was extracted from purified virions using a Qiaquick PCR purification kit (Qiagen) or a phenol/chloroform/proteinase K purification method (Sambrook, J. and R. D. W., "Preparation of Genomic DNA from Mouse Tails and Other Small Samples, Molecular Cloning, Cold Spring Harbor, N.Y., Cold Spring Harbor Laboratory Press, 1:6.23-6.27, 2001). DNA extracts from each fraction were run on 0.8% agarose gel and visualized by SYBR Green I (Sigma) staining. The copy number of encapsidated DNA was quantified with serially diluted standard DNA. Capsid proteins levels were measured by SDS-PAGE and silver staining with using defined dilutions of bovine serum albumin (BSA) as concentration standards (Table 2).

Infectivity assay. Infectivity of packaged HPV16 virions was examined by reverse transcriptase PCR (RT-PCR) by amplifying E1^E4 spliced mRNA signals from packaged HPV16-infected HaCaT cells. HaCaT cells were infected with dilutions of packaged virus overnight at 37° C., washed twice with PBS, and incubated for 48 hours at 37° C. Total RNA was isolated using the RNeasy total RNA purification kit (Qiagen) following the manufacturer's instructions, treated with RQ DNaseI (Promega) to remove possible DNA contaminants, purified again on RNeasy columns to remove DNaseI, and quantified by spectrophotometer. Double stranded cDNA was synthesized from 20 µg of total RNA with oligo (dT) using a SuperScript cDNA synthesis kit (Invitrogen), and PCR was performed with Taq DNA polymerase (Promega). Oligonucleotide primers (Table 1) were designed using the Primer3 primer design program (Rozen, S, and H. J. Skaletsky, "Primer3 on the WWW for General Users and For Biologist Programmers," Bioinformatics Methods and Protocols: Methods in Molecular Biology, Totowa, N.J., Humana Press, pp. 365-386, 2000), synthesized by MWG and used at 0.5 µM for PCR amplification for 36 cycles consisting of 1 minute at 94° C. for denaturation, 1 minute at 55° C. for annealing, and 2 minutes at 72° C. for polymerization, followed by 10 minutes at 72° C. for extension. For the following nested PCR, 2% of the first round PCR products were used in 30 cycles of amplification. The final PCR products were analyzed by 1% agarose gel electrophoresis and ethidium bromide staining.

To quantify the infectivity of pSEAP-encapsidating pseudovirus, a chemiluminescent assay for alkaline phosphatase was performed using the Phospha-Light System (Applied Biosystems). After adding the pSEAP pseudovirus, 293T cells were incubated for 48 hours. 50 µl of culture supernatant was collected and processed according to the manufacture's protocol, and luminescence was measured for 1 second in a luminometer.

Capsid disruption and virus neutralization. HPV capsids were disrupted by treating with 200 mM $NaHCO_3$, pH9.6 at 4° C. for 16 hours, followed by dialysis with PBS for 24 hours using SLIDE-A-LYZER dialysis cassette (Pierce). In parallel, an equal amount of virions was processed in PBS, pH7.0 as a control. HPV16-neutralizing antibodies H16.7E, H16.E70, and H16.V5 were obtained from Neil Christensen. Diluted virus preparations were incubated with one of the neutralizing antibodies at 1:100 dilutions for 1 hour at 4° C. with rotating before infecting human keratinocytes. Mouse non-neutralizing mouse anti-HPV16 L1 and anti-HIV-1 p24 (Chesebro, B., et al., *J. Virol.* 66(11):6547-6554, 1992; Toohey, K., et al., *Virology* 213(1):70-79, 1995; obtained through the AIDS research program, Division of AIDS, NIAID, NIH: HIV-1 p24 Monoclonal Antibody [(183-H12-5C)] from Dr. Bruce Chesebro and Kathy Wehrly) IgG antibodies were used for isotype controls. Non-neutralizing anti-HPV16 L1 antibody, H16.D9, is cross-reactive to HPV31 L1, but does not neutralize HPV16 capsid proteins (Christensen, N. D., et al., *Virology* 223(1):174-184, 1996).

Results

HPV16 genome package in L1/L2 capsid. Buck, et al. recently reported that the size of the target DNA packaged by papillomavirus capsid proteins L1 and L2 in 293TT cells was limited to less than 6 to 7 kb, so that a full length, ~8 kb HPV genome would not be efficiently encapsidated by this approach. To determine the size limit of HPV16 viral DNA encapsidation in our hands, we generated three progressively truncated derivatives of the HPV16 genome, with nested deletions in the L1 and L2 ORFs (FIG. 1B). In the smallest 5.0 kb derivative, the entire L1 and L2 ORFs were deleted leaving intact the LCR and early genes. The 5.9 kb HPV16 subgenomic clone retains the 3' portion of the L1 gene. The 6.8 kb subgenomic clone has an intact L1 ORF but is deleted for most of the L2 ORF. These HPV16 genome derivatives were amplified in *E. coli* plasmids, excised by XhoI digestion, recircularized by ligation, and transfected into 293TT cells. After 48 hours incubation, the cells were lysed, treated with endonuclease V to degrade unencapsidated viral and cellular DNA, and fractionated on OPTIPREP gradients. The results (FIG. 1B-D) showed that L1 and L2 expression protected all three truncated derivatives and full-length HPV genomic DNA from nuclease with equal efficiency, producing DNA bands that were visible by direct staining with the intercalating fluorescent stain, SYBR green 1, and that co-sedimented in gradients with authentic HPV capsids. No such DNA protection was observed if L1 and L2 expression was omitted (see also below). Western blotting (FIG. 1C) showed that L1 was distributed over a wider range of the gradient than was the DNA, with a major peak immediately above the sedimenting DNA (i.e. at a lower density), as expected for empty HPV capsids.

To measure the copy number of encapsidated HPV genome, DNA extracted from the packaged virus was analyzed by agarose gel electrophoresis, in comparison with HPV16 genomic DNA standards of known concentrations. From a transfection of one 10 cm 293TT cell dish, approximately $1.8 \times 10^9$ copies of nuclease-resistant HPV16 genomic DNA were encapsidated into HPV16 L1/L2 capsid proteins. To calculate the efficiency of HPV DNA encapsidation per capsid formed, the gradient-purified, packaged virus stock containing DNase-resistant DNA was analyzed by SDS-PAGE and the levels of HPV L1 and L2 proteins present were compared by silver staining to serially diluted BSA protein standards. These results showed that $\sim 8 \times 10^{10}$ assembled HPV particles were collected from one 10 cm dish of $\sim 7$ million cells, and that $\sim 3\%$ of these virus particles contained HPV16 genomic DNA. This efficiency of encapsidation is similar to that obtained when HPV particles are produced in organotypic cultures, in which 5-6% of the capsids contain HPV genomic DNA (Holmgren, S. C., Patterson, N. A., Ozbun, M. A., and Lambert, P. F. The Minor Capsid Protein, L2, Contributes to Two Steps in the HPV31 Life Cycle. *Journal of Virology*, in press, 2004, Exhibit A). However, such organotypic cultures yield in the range of only $10^7$ particles in total. Thus, our results show that transfection of a single 10 cm dish of cells yielded in 2 days yields over 1000 times more HPV DNA-containing virions than a two-week organotypic raft culture (Table 2).

To test whether different HPV genotypes could be packaged by the same method, we co-transfected full length, recircularized HPV31b genomic DNA along with pXULL into 293TT cells, and found that these HPV31 genomes also were efficiently packaged into HPV16 L1/L2 capsids (data not shown). Thus, the results are not HPV16-specific, and the same approaches can be applied to produce virions of other HPV genotypes.

Infectivity of packaged HPV16. The infectivity of the 293TT cell-packaged HPV16 virions was tested in HaCaT cells, an immortalized human keratinocyte cell line. 48 hours after inoculation, cells were harvested, total RNA was purified, and RT-PCR was performed to detect one of the spliced viral mRNAs, an established measure for HPV infectivity (White, W. I., et al., *J. Virol.* 72:959-964, 1998; Ozbun, M. A., *J. Virol.* 76:11291-11300, 2002; Ozbun, M. A., *J. Gen. Virol.* 83:2753-2763, 2002). The expected PCR product from the E1^E4 spliced mRNA was seen (FIG. 2A), showing that the virus particles generated using the transient transfection based method were infectious.

To confirm that viral gene expression detected in the infection assay did not arise wholly or partially from direct transfection of naked DNA not packaged by HPV16 capsid proteins, we treated virus stocks with 200 mM NaHCO$_3$, pH 9.6, which efficiently and irreversibly disrupts HPV capsids. Following treatment, the preparations were dialyzed against PBS and added to HaCaT cells. This pre-treatment of virus stocks at high pH abolished viral mRNA expression in inoculated HaCaT cells, while untreated, but dialyzed, control HPV16 retained a strong E1^E4 mRNA expression signal (FIG. 2A). In parallel, we inoculated HaCaT cells with 0.1 µg of unencapsidated HPV16 genomic DNA, a 200-fold excess over the level of HPV16 DNA in the gradient-purified, DNase-treated virion preparations that successfully initiate infection. As expected, even this great excess of unencapsidated HPV16 genomic DNA did not lead to any PCR-detectable expression of E1^E4 mRNA (FIG. 2A), showing that successful infection and viral gene expression under these conditions require HPV16 DNA encapsidation.

To further validate that we were producing infectious HPV particles, we monitored the effect of pre-treating the HPV16 virion preparations with L1-speciifc HPV16 neutralizing antibodies, H16.7E, H16.E70, and H16.V5 (all antibodies were obtained from Neil Christensen at the Pennsylvania State University), before inoculating HaCaT cells. Each of these neutralizing antibodies efficiently blocked the ability of the HPV preparations to induce E1^E4 mRNA expression, while virus incubated with nonspecific isotype control antibodies such as non-neutralizing anti-HPV16 µl and anti-HIV p24 antibodies, showed unimpaired infectivity (FIG. 2B). Thus, the susceptibility of our infectious preparations from HPV DNA-transfected 293TT cells to chemical disruption and highly specific neutralizing antibodies paralleled that of natural HPV virions.

Equal infectivity of HPV16 W12 and 114B. HPV16 subtype W12, although the HPV genotype most commonly used in research, does not produce infectious virions in organotypic raft culture (Dollard, S. C., et al., *Genes Dev.* 6(7):1131-1142, 1992; Meyers, C., et al., *Science* 257(5072):971-973, 1992; McLaughlin-Drubin, M. E., et al., *Virology* 312(1):1-7, 2003; McLaughlin-Drubin, et al., *Virology* 322(2): 213-219, 2004). In contrast, two other HPV16 variants, 114B and 114K, readily produced infectious virions in the organotypic raft culture, suggesting that potentially small sequence differences between W12 and 114B or 114K cause major alterations in virus infectivity. To examine the source of such differences in infectivity of HPV16 variants, we packaged the excised, recircularized genomes of HPV16 W12 and 114B variants into HPV16 prototype capsid proteins, purified virions by Optiprep gradients, and inoculated HaCaT cells as before. All of the resulting viruses, bearing the genomes of the HPV16 W12 and 114B variant showed equal infectivity on HaCaT cells (FIG. 2A).

Figure 3:
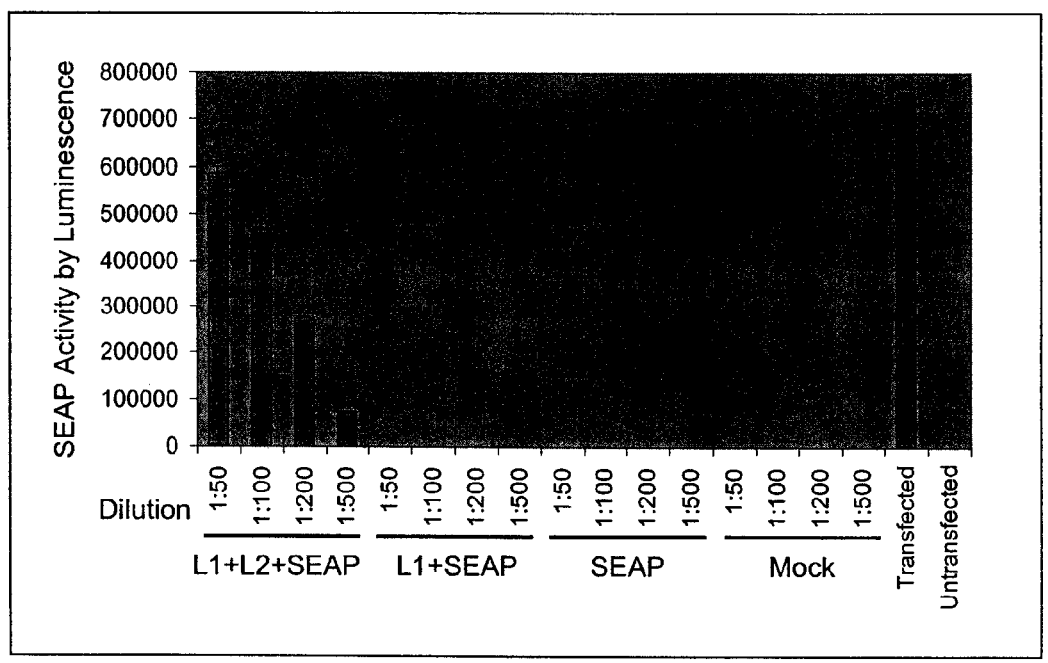
FIG. 3. Quantification of 293TT cell-packaged HPV16 pseudovirions. A reporter plasmid, pSEAP-control, encapsidated pseudovirions (FIG. 1D) were inoculated into 293T cells at four different dilutions and incubated for 48 hours. Cell culture supernatants were used for alkaline phosphatase activity assays described in materials and methods. One μg of pSEAP-control DNA was transfected using Lipofectamine 2000 as a positive control.

Gene delivery and expression efficiency of HPV capsids. To measure the efficiency of gene delivery and expression by HPV capsids, we used pSEAP, a plasmid expressing secreted alkaline phosphatase, as a target for HPV16 packaging and used the resulting pseudovirions to infect 293T epithelial cells. The resulting SEAP activity was nearly linear with dilution of the infecting pseudovirus stock over the range tested, retaining substantial activity $\sim 700$-fold above background after 500-fold dilution (FIG. 3). In particular, SEAP activity after infection with $\sim 1.5 \times 10^8$ copies of encapsidated pSEAP DNA was nearly as high as that in 293T cells after Lipofectamine 2000 transfection with $\sim 3.4 \times 10^{11}$ copies of unencapsidated pSEAP DNA. Thus, DNA encapsidation into HPV capsid proteins increased the efficiency of gene delivery and expression at least 2000-fold relative to even efficient transfection methods. In HaCaT cells, alkaline phosphatase background activity was too high to measure meaningful SEAP activity in the virus infected cell culture supernatant.

Discussion

HPVs are of major clinical importance because they are the most common sexually transmitted pathogen and cause prevalent human cancers. The dependence of HPV replication to epithelial cell differentiation has greatly limited the ability to produce infectious HPV needed for both basic and clinical research on these viruses. Here, we have described a facile method for efficiently producing large quantities of HPV particles that display normal infectious properties. This method offers dramatic advantages over prior methods such as organotypic cultures by providing over a 1000-fold increased yield of virus in a much shorter period of time. Virus of any desired genotype can be generated, and furthermore, because there is no reliance upon the replication of the viral genome in the cells in which packaging occurs, one can encapsidate HPV DNAs bearing essentially any desired mutation.

In this report, we showed evidence that infectivity of the 293TT cell-packaged HPV represents actual HPV virions. When infected with 293TT cell-packaged HPV16 virions, HaCaT cells expressed E1^E4 spliced early mRNA detectable by RT-PCR as established HPV16 expressing W12 cell lines (FIG. 2A). Capsid disruption by high pH carbonate buffer or neutralization by specific antibodies efficiently abolished HPV16 early gene expression (FIGS. 2A, B), suggesting that these infections were exclusively dependent on HPV L1 and L2 capsid proteins.

Full-length HPV DNA packaging. Contrary to the original transient transfection based study in which it was documented that the efficiency with which BPV-1 capsids could encapsidate target DNAs fell off rapidly for target DNAs larger than 6 kb (Buck, C. B., et al., *J. Virol.* 78:751-757, 2004), we found that full length, 7.9 kb HPV16 and HPV31 genomes were incorporated into HPV16 L1 and L2 capsid proteins as efficiently as 5 to 7 kb deletion derivatives (FIG. 1B) or smaller reporter plasmids. This suggests either that HPV16 based capsids produced in our hands have different packaging constraints than do the BPV1 capsids produced in the earlier study, or that differences in the nature of the DNA being packaged contributes to differences in packaging efficiency. The latter possibility could reflect the presence of packaging signals in the HPV genome that permit for efficient packaging of full length or near full-length genomes. A region of the BPV1 genome has been described to contribute to DNA encapsidation; however, Buck and Schiller found this region of the BPV1 genome to confer only a modest increase in packaging efficiency in the BPV1 L1/L2 based, transient-transfection based assay. Thus, while Buck, et al. suggested that in vivo encapsidation by papillomavirus capsid proteins is promiscuous with respect to target DNA sequence and driven primarily by a size discrimination mechanism that was predicted to greatly limit the encapsidation efficiency of full-length viral genomes, our results indicate that size discrimination does not prevent efficient encapsidation of full-length HPV genomes in the system as established in our hands.

Although HPV16 is the most prevalent genotype in HPV pathogenesis and oncogenesis, other HPVs including high risk and low risk mucosotropic virus such as HPV6. 11 18 and 31 are of clinical importance because they cause sexually transmitted disease, and for the high risk genotypes, cancer. Thus, it would also be valuable if a single approach could produce infectious virions for multiple HPV genotypes. Toward this end we demonstrate that we were able to generate infectious HPV16 L1/L2 virus particles harboring either different variants of encapsidated HPV16 or an alternative HPV genotype, HPV31. Furthermore, this transient transfection based system described herein could be used to produce virtually any papillomavirus of interest in high yield, given that L1 and L2 proteins of other papillomaviruses tested all can self-assemble into capsid particles, because highly efficient expression of papillomaviral proteins in mammalian cells can now be routinely achieved using codon optimized versions of the cognate genes. In addition to providing infectious virus for basic research studies on other papillomavirus genotypes, such infectious HPV stocks would be highly useful for evaluating the successful generation of neutralizing abs to other genotypes in preclinical and clinical vaccine studies.

Other sample applications of infectious HPV virions. HPV16 subtype W12, the genotype most commonly used in basic research, has not yielded infectious virions in organotypic raft culture, while HPV16 variants 114B and 114K readily produce infectious virions under these conditions (McLaughlin-Drubin, M. E., et al., supra, 2004). The reason for these infectivity differences is unclear. Here, we found that HPV16 W12, 114K, and 114B DNAs produced equally infectious virions when encapsidated into HPV16 114K capsid proteins. This suggests that the varied infectivity of these HPV16 variants may be due to differences in their capsid proteins rather than their early gene products or cis-acting functions. Accordingly, we are generating chimeric L1/L2 expression plasmids exchanging selected L1 and L2 coding regions between HPV16 variants, to determine whether and, if so, which differences in L1 and L2 control these infectivity differences.

Similarly, to optimize and improve prophylactic HPV vaccines, mutagenesis and selection of infectious HPV virions could be used to identify neutralizing epitopes present in sera of patients or HPV vaccines.

The abilities presented here to rapidly produce infectious HPV virions in large amounts and, moreover, to incorporate essentially any desired mutation in the HPV DNA so packaged, make possible previously unapproachable studies of virus-host interactions in early phases of the HPV life cycle. For example, while some potential cellular receptors for HPV entry have been identified, their potential relevance to establishment of clinical HPV infections remains controversial. The procedures described here would allow for biochemical testing of virus attachment to various candidate cell surface receptors using infectious particles, as well as mutagenesis to map and characterize cell binding motifs in HPV capsid proteins. In addition, wt or suitably marked HPV derivatives could be used with the methods presented here in genetic screens to identify critical host factors for virus entry, and also for subsequent steps leading to early gene expression, such as uncoating, virion protein-mediated HPV DNA trafficking to nucleus, initial transcription, etc. Understanding these mechanisms would identify novel therapeutic targets for antiviral drug development.

Another important advantage is that, since the procedures described here encapsidate HPV genomes directly isolated from bacteria, such DNAs would contain bacterially-directed Dam and Dcm methylation. Since mammalian host cells lack such methylation, this allows ready discrimination by methylation-specific restriction enzymes between the infecting HPV founder genomes and subsequently replicated copies. This approach would facilitate studies of early steps in viral DNA replication about which little is presently known.

Current HPV vaccine strategies are directed to raising neutralizing antibodies to prevent initial HPV infection. The approaches described here open the possibility of producing live, attenuated HPV vaccines to trigger both humoral and cell-mediated immune responses. Such cell-mediated immune responses, including cytotoxic T-cell activation, provide much more effective prophylaxis against most viral infections and also offer therapeutic potential for the large numbers of patients already infected with HPV. The ability to package HPV genomes with engineered changes into infectious HPV virions also will allow studying further important aspects of immune responses to HPV. Some HPV16 early genes such as E7 have been reported to have immunosuppressive effects (Barnard, P. and N. A. McMillan, Virology 259 (2):305-313; 1999; Borchers, A., et al., *Arch. Virol.* 144(8): 1539-1556, 1999), implying that host immune responses against intact infectious HPV might differ radically from those against empty HPV capsids. Such differences can now be evaluated.

TABLE 1

Oligonucleotide primers used in HPV16 infectivity assays.

| Primer name | Sequence | Direction | Position |
|---|---|---|---|
| 16E7.5U | 5'-TTTGCAACCAGAGACAACTGAT (SEQ. ID NO: 5) | Sense | 603-624 |
| 16E7.5L | 5'-AGAGGCTGCTGTTATCCACAAT (SEQ. ID NO: 6) | Antisense | 3993-4014 |
| 16E7.5UN | 5'-AAATGACAGCTCAGAGGAGGAG (SEQ. ID NO: 7) | Sense | 645-666 |
| 16E7.5LN | 5'-TGTTAAATGCAGTGAGGATTGG (SEQ. ID NO: 8) | Antisense | 3551-3572 |
| 31E7.5U | 5'-ATGAGCAATTACCCGACAGC (SEQ. ID NO: 9) | Sense | 633-652 |
| 31E7.5L | 5'-GCACACAAAAGCAAAGCAAA (SEQ. ID NO: 10) | Antisense | 3860-3879 |
| β-actin-U | 5'-CCAAGGCCAACCGCGAGAAGATGACC (SEQ. ID NO: 11) | Sense | 445-471 |
| β-actin-L | 5'-CCACATCTGCTGGAAGGTGGACAGCG (SEQ. ID NO: 12) | Antisense | 1154-1179 |

TABLE 2

Comparison between 293TT cell culture and organotypic raft culture for HPV preparations.

|  | 293TT culture | Raft culture |
|---|---|---|
| Time | 2 days | 21 days |
| Yield (encapsidated HPV genomes per preparation) | $2 \times 10^9$ copies | $1 \times 10^6$ copies |

Figure 4:
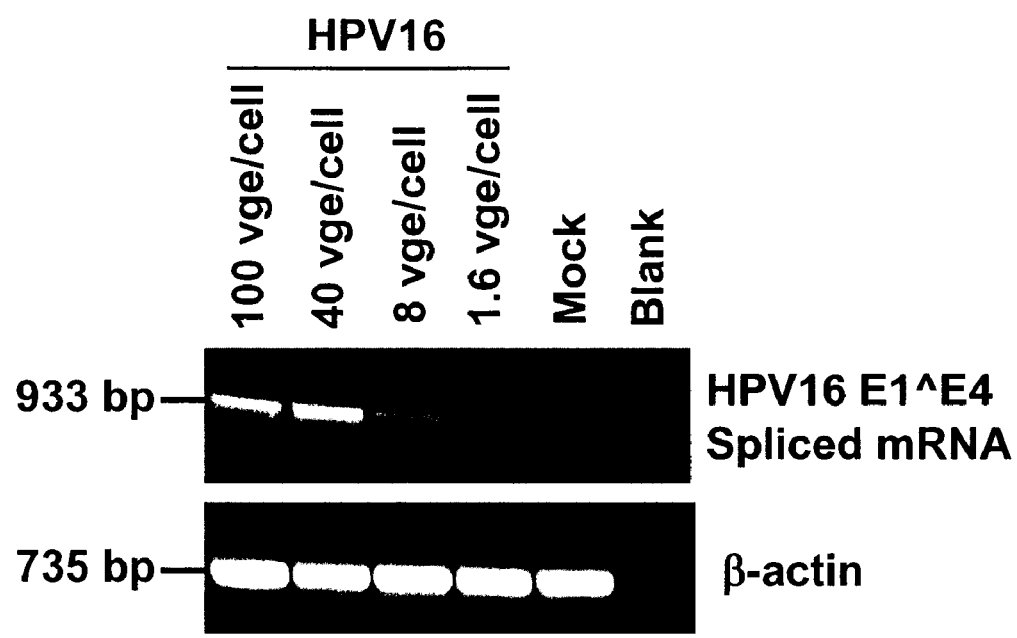
FIG. 4. Infectivity of encapsidated, full-length HPV16 DNA. Virions encapsidating the HPV16 W12 genome were produced and inoculated onto HaCaT cells. At 48 h after inoculation, cells were harvested, total RNA was isolated, and a single round of RT-PCR or RT-PCR was performed with PCR primers (Table 1) to detect E1^E4 spliced mRNAs. We amplified β-actin mRNA simultaneously as an internal standard. Cells were inoculated with 100 to 1.6 vge per cell as indicated and assayed for infection by single round RT-PCR.

II. The Specific Infectivity of 293T-Packaged HPV is Comparable to Infectivity of Raft Culture-Prepared HPV The infectivity of the HPV16 virions that were produced in 293TT cells was tested in HaCaT cells, an immortalized human keratinocyte cell line. 48 h after inoculation, cells were harvested, total RNA was purified, and RT-PCR was performed to detect one of the spliced viral mRNAs, an established measure for HPV infectivity. The expected PCR product from the E1^E4 spliced mRNA was seen (FIG. 4), showing that the virus particles generated using the transient transfection based method were infectious. Infection with 100- to 6250-fold serial dilutions of the starting virus stock, corresponding to 100 to 1.6 HPV16 viral genome equivalents (vge)/cell revealed that less than 10 vge/cell of virion stock from 293TT cell transfection still clearly showed detectable infection by single round RT-PCR (FIG. 4). This result further confirms that the yield of virus, as measured above by the quantity of DNase resistant viral genomes present in Optiprep-fractionated virus stock, was over 1000-fold greater than the amount of virus typically obtained from rafts while the specific infectivity is comparable. The materials and methods were as described above for Example I.

III. Desired Mutations can be Incorporated in Packaged HPV

To examine the minimum HPV16 genome sequence required for early gene expression, we infected HaCaT cells with virion particles containing the 5.0 kb, 5.9 kb, and 6.8 kb HPV16 genome derivatives. All three derivatives showed expression of E1^E4 spliced mRNA in HaCaT cells (FIG. 5A), while HPV31b- and mock-infected did not, suggesting that any of HPV16 L1 and L2 ORF sequences are not necessary for early viral gene transcription. The materials and methods were as described above for Example I.

IV. Multiple HPV Genotypes can be Packaged

Figure 5:
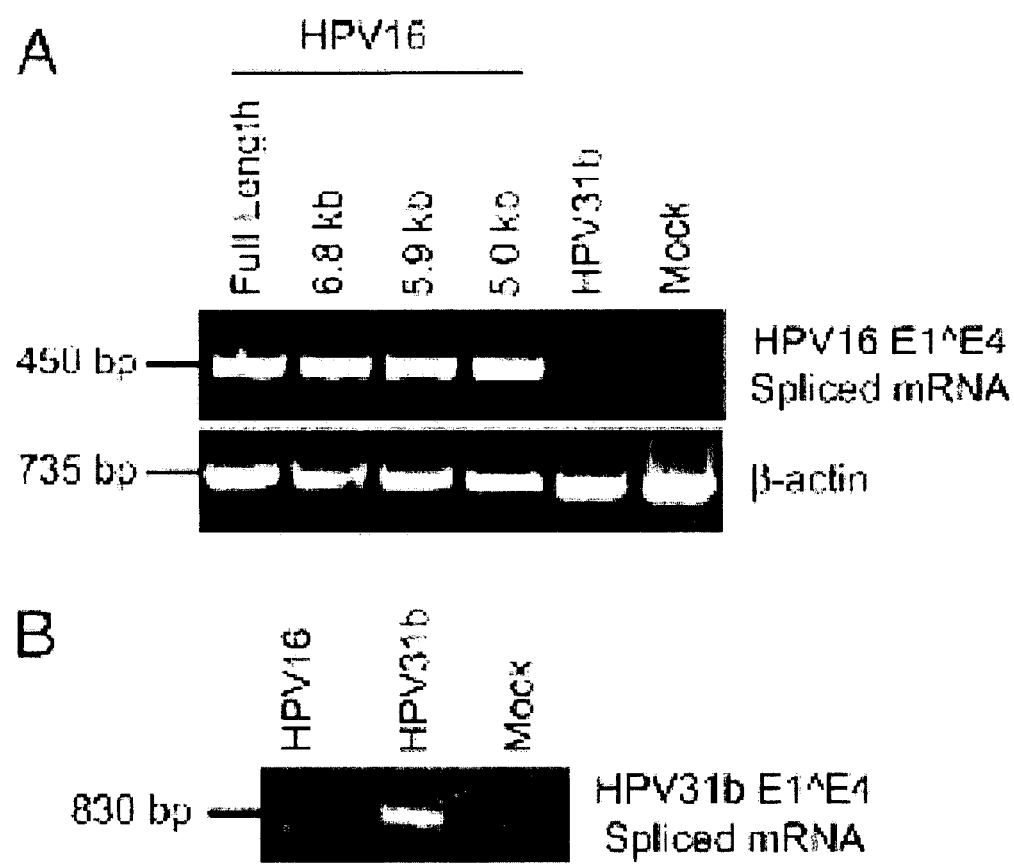
FIG. 5. Induction of early gene expression by encapsidated HPV16 genome derivatives and infectivity of encapsidated, full-length HPV31b genomic DNA. Virions were prepared as described by cotransfecting HPV16 L1- and L2-expression plasmids and either the HPV16 genome deletion derivatives of FIG. 1A (FIG. 5A) or the HPV31b full-length genome (FIG. 5B), and they were inoculated onto HaCaT cells at 100 vge per cell. After a 48-h incubation, cells were harvested, total RNA was isolated, and nested RT-PCR was performed with PCR primers to detect E1^E4 spliced mRNAs of HPV16 (FIG. 5A) or HPV31b (FIG. 5B) (see Table 1).

Nuclease treatment and gradient fractionation showed that HPV16 L1 and L2 capsid proteins also encapsidated the full-length HPV31b genomic DNA. To test the infectivity of HPV31b genome packaged in HPV16 virus particles, we added these chimeric virions to HaCaT cells and performed RT-PCR with HPV31b-specific primers. The expected signal for the E1^E4 spliced mRNA of HPV31b was revealed from extracted total RNA by one round amplification, while HaCaT cells infected with virions made by co-transfecting L1 and L2 expression plasmids with full-length HPV16 genomes or no HPV genomic DNA did not express HPV31b RNA transcripts (FIG. 5B). These results indicate that mammalian cell transfection for HPV packaging is not restricted to one genotype, but could be applied to other high and low risk HPV genotypes.

Figure 6:
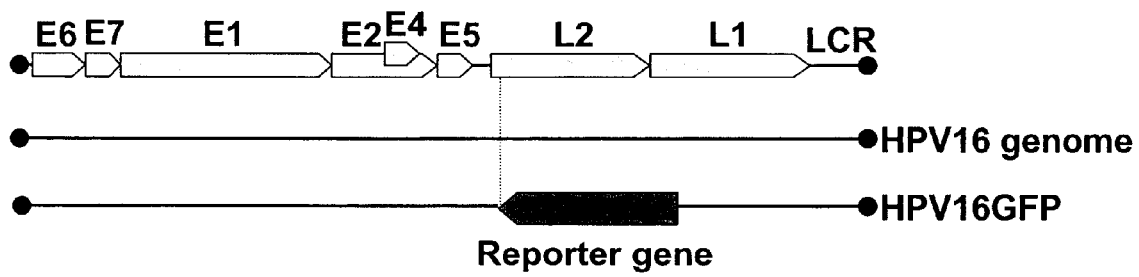
FIG. 6. Reporter gene expression from HPV16-reporter chimeric genome driven by various promoters. Each reporter gene (SEAP, RL, and GFP) was cloned with one of the following promoters: Tet-responsive element, thymidine kinase promoter, or SV40 promoter and incorporated into late gene region of HPV16 genome (4295-6277) (FIG. 6A). Virion particles were isolated as described above. SEAP activity was measured after two day infection in 293TT cells. For expression by TRE, pTet-On plasmid was transfected 16 h prior to virus infection and gene expression was induced by doxycycline 6 hrs after infection. Successful infection is shown by SEAP (FIG. 6B) and GFP (FIG. 6C) expression. GFP-expressing cells were lysed, total RNA was extracted, and HPV16 E1^E4 expression was determined as previously described (FIG. 6D). Virion particles were prepared with cloned pHPV16RL-TRE and HPV16 L1/L2 expressing plasmids. Normal human keratinocytes, HaCaT cells, were transfected with pTet-On plasmid overnight and randomly infected with intact virions or neutralized virions in 96-well screening plates. After 6 h incubation, RL expression was induced with doxycycline for 48 h. Luciferase activity was measured using *Renilla* Luciferase assay system (Promega) (FIG. 6E).
Figure 6:
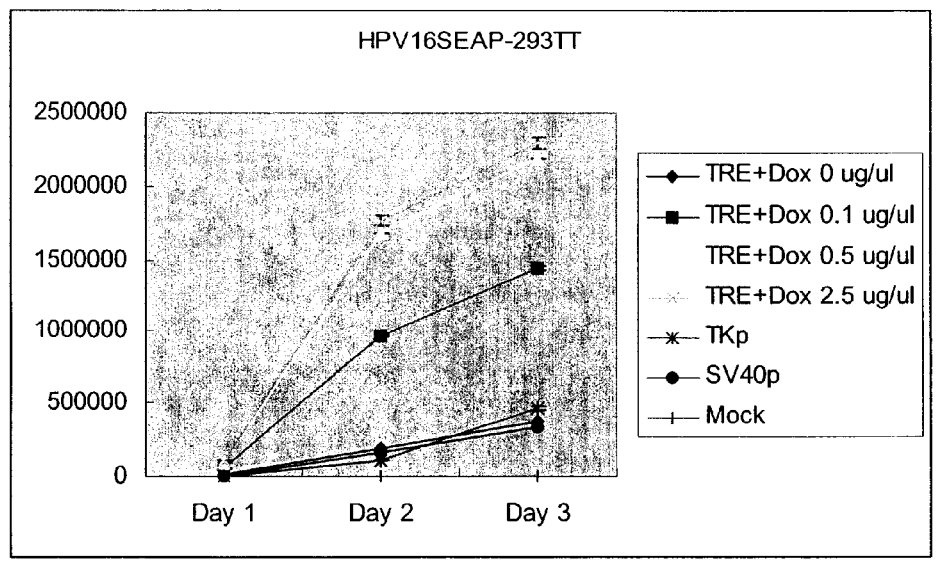
Figure 6:
Figure 6:
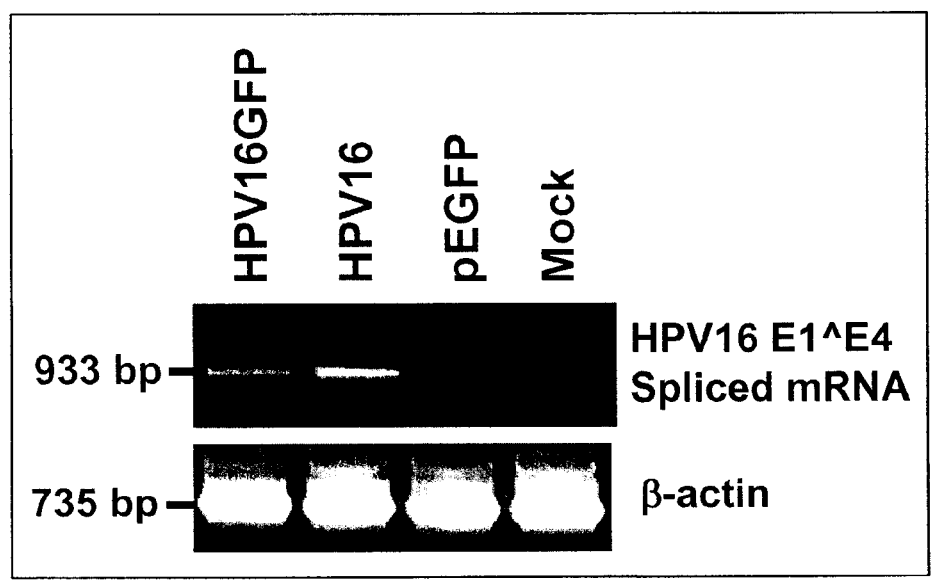
Figure 6:
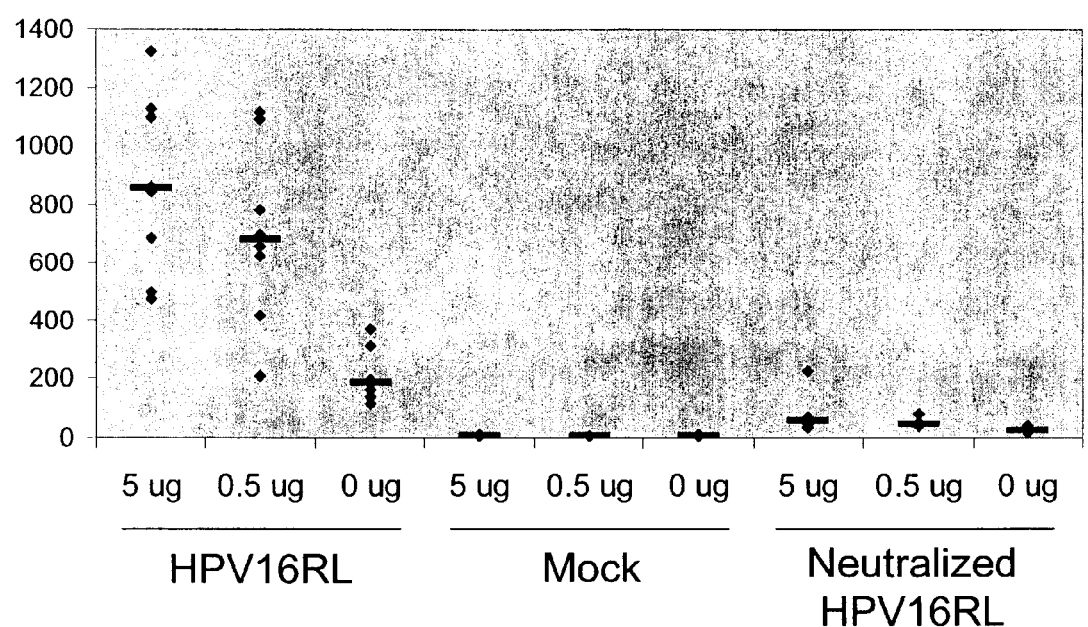

V. High Throuput Screening System Using 293T-Packaged HPV16-Reporter Chimeric DNA To express reporter genes from HPV genome backbone and examine HPV-infected individual cells, we cloned reporter genes with constitutive or inducible promoters into late gene region of HPV16 genome. Since activity of the CMV early promoters used for HPV capsid protein expression was significantly abrogated when another construct containing the same CMV early promoter was cotransfected, we could not use CMV early promoter to express a reporter gene in HPV16, packaged by pXULL and pcDNA-HPV16 L1/L2 constructs in 293T transfection. Thus, we tested workable promoters in normal epithelial cells with 293T packaging system. Various promoters, such as the SV40 promoter, the human simplex virus thymidine kinase (HSV-TK) promoter, and the tetracycline-responsive element (TRE), were cloned into HPV16 genome with reporter genes such as renillar luciferase (RL), secreted alkaline phosphatase (SEAP), and green fluorescent protein (GFP). Each reporter gene cloned with one of the promoters was inserted to the L1 and L2 region (4295-6277) of HPV16 genome in the opposite transcription direction from the HPV16 early genes (FIG. 6A). These chimeric constructs were packaged into HPV16 capsid structure using the 293T packaging system as previously described. All the constructs were successfully packaged in HPV16 capsid proteins.

To determine reporter activity in infected cells, HPV16 chimeric pseudovirions were transduced into 293T cells. The reporter assay showed that all the promoters successfully activated reporter gene expression (FIGS. 6B and C), while HPV16 early genes were also expressed in same infected cells (FIG. 6D), indicating that HPV16-infected cells could be quantitatively detected by reporter activity. However, HaCaT cells did not support SV40 promoter activity at all and also showed relatively lower HSV-TK promoter activity (data not shown). In contrast, TRE efficiently induced reporter gene expression in HaCaT cells and was also easily regulated by doxycycline in post-transfection (FIG. 6E).

Using the HPV16-reporter pseudovirions, we developed a high throughput screening (HTS) system to identify host genes as well as small molecules which block HPV early infection step(s) including virus attachment, entry, gene delivery, and gene expression.

Our preliminary screening suggests that luciferase activity from successful infection is sufficiently high to be distinguished from negative controls pre-treated with neutralizing antibody H16.7E (FIG. 6E).

Since genetic screening requires transfection of siRNA or cDNA, normalization of transfection efficiency is necessary. However, transfection efficiency of normal keratinocytes such as HaCaT is extremely low so that normalization step could be problematic in a large number of samples in HTS. In our assay system, pTet-On (Clontech), which expresses the reverse tetracycline-responsive transcriptional activator and cooperates with doxycycline to activate TRE activity, could be cotransfected with each siRNA or cDNA of libraries, and consequently, only transfected cells would trigger reporter gene expression. This unique feature will give a big advantage during HTS, removing cumbersome transfection normalization steps.

Materials & Methods

Each reporter gene (SEAP, RL, and GFP) was cloned with one of the following promoters: Tet-responsive element, thymidine kinase promoter, or SV40 promoter and incorporated into late gene region of HPV16 genome (4295-6277). SEAP, RL, and GFP were originated from pSEAP-control (Clontech), phRL-null (Promega), pEGFP-N3 (Clontech), respectively. The constructed DNA was packaged in HPV16 L1/L2 capsid proteins as described previously. After 2 d infection, culture supernatant (SEAP) or cell lysate (RL) was harvested and reporter assay was performed using PhosphaLight SEAP Assay system (Applied Biosystems) or Renilla Luciferase Assay System (Promega). Images of GFP-expressing cells were captured using fluorescence microscope (Axiovert, Zeiss) and analyzed by Adobe Photoshop.

REFERENCES

| HPV Genotype | Genbank Accession |
|---|---|
| 16 | NC_001526 |
| 18 | X05015 |
| 31 | J04353 |
| 6 | X00203 |
| 11 | M14119 |
| 32 | X74475 |
| 33 | M12732 |
| 38 | U31787 |
| 45 | X74479 |
| 58 | D90400 |
| 12 | X74466 |
| 13 | X62843 |
| 17 | X74469 |
| 22 | U31780 |
| 30 | X74474 |
| 34 | X74476 |
| 35 | X74477 |
| 39 | M62849 |
| 42 | M73236 |
| 43 | M27022, U12504 |
| 44 | U31788 |
| 51 | M62877 |
| 52 | X74481 |
| 53 | X74482 |
| 54 | U37488 |
| 55 | U31791 |
| 56 | X74483 |
| 57 | X55965 |
| 59 | X77858 |
| 61 | U31793 |
| 66 | U31794 |
| 67 | D21208 |
| 68 | M73258 |
| 69 | U12497 |
| 70 | U21941 |
| 72 | X94164 |
| 5 | M17463, M22961 |
| 8 | M12737 |

| Animal PV Genotype | Genbank Accession |
|---|---|
| Canine oral papillomavirus (COPV) | L22695 |
| Rhesus papillomavirus type 1 (RHPV1) | M60184 |
| Cottontail rabbit papillomavirus (CRPV) | NC_001541 |
| Rabbit oral papillomavirus (ROPV) | U09494 |

Author: Baker, C. C.
Title: The Genomes of the Papillomaviruses
Journal: (in) O'Brien, S. J. (Ed.); Genetic Maps; Locus Maps of Complex Genomes: 1-1, Cold Spring Harbor Laboratory Press, Cold Spring Harbor (1993)
HPV16
Author: Seedorf, K., Kraemmer, G., Duerst, M., Suhai, S, and Roewekamp, W. G.
Title: Human papillomavirus type 16 DNA sequence
Journal: Virology 145, 181-185 (1985)
Medline: 85246220
HPV18
Author: Cole, S. T. and Danos, O.

Title: Nucleotide sequence and comparative analysis of the human papillomavirus type 18 genome
Journal: J. Mol. Biol. 193, 599-608 (1987)
Medline: 87283882
HPV31
Author: Goldsborough, M. D., DiSelvestre, D., Temple, G. F. and Lorincz, A. T.
Title: Nucleotide sequence of human papillomavirus type 31: A cervical neoplasia associated virus
Journal: Virology 171, 306-311 (1989)
Medline: 89299478
HPV6
Author: Schwarz, E., Duerst, M., Demankowski, C., Lattermann, O., Zech, R., Wolfsperger, E., Suhai, S, and Zur Hausen, H.
Title: DNA sequence and genome organization of genital human papillomavirus type 6b
Journal: EMBO J. 2, 2341-2348 (1983)
Medline: 84131949
HPV11
Author: Dartmann, K., Schwarz, E., Gissmann, L. and Zur Hausen, H.
Title: The nucleotide sequence and genome organization of human papilloma virus type 11
Journal: Virology 151, 124-130 (1986)
Medline: 86181601
HPV32
Author: Delius, H. and Hofmann, B.
Title: Primer-directed sequencing of human papillomavirus types
Journal: Curr. Top. Microbiol. Immunol. 186, 13-31 (1994)
Medline: 94265501
Author: Beaudenon S, Praetorius F, Kremsdorf D, Lutzner M, Worsaae N, Pehau-Arnaudet G, Orth G
Title: A new type of human papillomavirus associated with oral focal epithelial hyperplasia
Journal: J Invest Dermatol. 1987 February; 88(2):130-5.
Medline: 87110804
HPV33
Author: Cole, S. T. and Streeck, R. E.
Title: Genome organization and nucleotide sequence of human papillomavirus type 33, which is associated with cervical cancer
Journal: J. Virol. 58, 991-995 (1986)
Medline: 86200464
HPV38
Author: Scheurlen, W., Gissmann, L., Gross, G., and zur Hausen, H.
Title: Molecular cloning of two new HPV types (HPV 37 and HPV 38) from a keratoacanthoma and a malignant melanoma.
Journal: International Journal of Cancer 37(4), 505-510 (1986)
Medline: 86166976
HPV45
Author: Naghashfar Z S, Rosenshein N B, Lorincz A T, Buscema J, Shah K V
Title: Characterization of human papillomavirus type 45, a new type 18-related virus of the genital tract
Journal: J Gen Virol. 1987 December; 68 (Pt 12):3073-9.
Medline: 88089509
HPV58
Author: Kirii, Y., Iwamoto, S.-I. and Matsukura, T.
Title: Human papillomavirus type 58 DNA sequence
Journal: Virology 185, 424-427 (1991)
Medline: 92024102
HPV12
Author: Delius, H. and Hofmann, B.
Title: Primer-directed sequencing of human papillomavirus types
Journal: Curr. Top. Microbiol. Immunol. 186, 13-31 (1994)
Medline: 94265501
Author: Delius, H.
Title: Direct Submission
Journal: Submitted (6 Aug. 1993) to the EMBL/GenBank/DDBJ databases. H. Delius, Deutsches Krebsforschungszentrum, Abteilung ATV, Im Neuenheimer Feld 506, W 6900 Heidelberg, FRG
HPV13
Author: Van Ranst, M., Fuse, A., Fiten, P., Beuken, E., Pfister, H., Burk, R. D. and Opdenakker, G.
Title: Human papillomavirus type 13 and pygmy chimpanzee papillomavirus type 1: Comparison of the genome organizations
Journal: Virology 190, 587-596 (1992)
Medline: 92391075
HPV17
Author: Delius, H. and Hofmann, B.
Title: Primer-directed sequencing of human papillomavirus types
Journal: Curr. Top. Microbiol. Immunol. 186, 13-31 (1994)
Medline: 94265501
Author: Delius, H.
Title: Direct Submission
Journal: Submitted (6 Aug. 1993) to the EMBL/GenBank/DDBJ databases. H. Delius, Deutsches Krebsforschungszentrum, Abteilung ATV, Im Neuenheimer Feld 506, W 6900 Heidelberg, FRG
HPV22
Author: Kremsdorf, D., Favre, M., Jablonska, S., Obalek, S., Rueda, L. A., Lutzner, M. A., Blanchet-Bardon, C., Van Voorst Vader, P. C., and Orth, G.
Title: Molecular cloning and characterization of the genomes of nine newly recognized human papillomavirus types associated with epidermodysplasia verruciformis
Journal: Journal of Virology 52(3), 1013-1018 (1984)
Medline: 85033930
HPV30
Author: Kahn T, Schwarz E, zur Hausen H
Title: Molecular cloning and characterization of the DNA of a new human papillomavirus (HPV 30) from a laryngeal carcinoma
Journal: Int J Cancer. 1986 Jan. 15; 37(1):61-5.
Medline: 86084580
Author: Bergeron C, Barrasso R, Beaudenon S, Flamant P, Croissant O, Orth G
Title: Human papillomaviruses associated with cervical intraepithelial neoplasia. Great diversity and distinct distribution in low- and high-grade lesions
Journal: Am J Surg Pathol. 1992 July; 16(7):641-9.
Medline: 92411377
HPV34
Author: Kawashima M, Jablonska S, Favre M, Obalek S, Croissant O, Orth G
Title: Characterization of a new type of human papillomavirus found in a lesion of Bowen's disease of the skin
Journal: J Virol. 1986 February; 57(2):688-92.
Medline: 86115420
HPV35
HPV35
Author: Delius, H. and Hofmann, B.
Title: Primer-directed sequencing of human papillomavirus types
Journal: Curr. Top. Microbiol. Immunol. 186, 13-31 (1994)

Medline: 94265501
Author: Delius, H.
Title: Direct Submission
Journal: Submitted (6 Aug. 1993) to the EMBL/GenBank/ DDBJ databases. H. Delius, Deutsches Krebsforschungszentrum, Abteilung ATV, Im Neuenheimer Feld 506, W 6900 Heidelberg, FRG HPV39
Author: Volpers, C. and Streeck, R. E.
Title: Genome organization and nucleotide sequence of human papillomavirus type 39 Journal: Virology 181, 419-423 (1991)
Medline: 91135017

HPV42
Author: Philipp, W., Honore, N., Sapp, M., Cole, S. T. and Streeck, R. E.
Title: Human papillomavirus type 42: New sequences, conserved genome organization
Journal: Virology 186, 331-334 (1992)
Medline: 92087479

HPV43
Author: Lorincz, A. T., Quinn, A. P., Goldsborough, M. D., Schmidt, B. J. and Temple, G. F.
Title: Cloning and partial DNA sequencing of two new human papillomavirus types associated with condylomas and low-grade cervical neoplasia
Journal: J. Virol. 63, 2829-2834 (1989)
Medline: 89259065
Author: Lorincz A T, Reid R, Jenson A B, Greenberg M D, Lancaster W, Kurman R J
Title: Human papillomavirus infection of the cervix: relative risk associations of 15 common anogenital types
Journal: Obstet Gynecol. 1992 March; 79(3):328-37.
Medline: 92149946

HPV44
Author: Lorincz, A. T., Quinn, A. P., Goldsborough, M. D., Schmidt, B. J. and Temple, G. F.
Title: Cloning and partial DNA sequencing of two new human papillomavirus types associated with condylomas and low-grade cervical neoplasia
Journal: J. Virol. 63, 2829-2834 (1989)
Medline: 89259065

HPV51
Author: Lungu, O., Crum, C. P. and Silverstein, S. J.
Title: Biologic properties and nucleotide sequence analysis of human papillomavirus type 51
Journal: J. Virol. 65, 4216-4225 (1991)
Medline: 91303675

HPV52
Author: Shimoda K, Lorincz A T, Temple G F, Lancaster W D
Title: Human papillomavirus type 52: a new virus associated with cervical neoplasia
Journal: J Gen Virol. 1988 November; 69 (Pt 11):2925-8.
Medline: 89036173

HPV53
Author: Gallahan D, Muller M, Schneider A, Delius H, Kahn T, de Villiers E M, Gissmann L
Title: Human papillomavirus type 53
Journal: J Virol. 1989 November; 63(11):4911-2.
Medline: 90012350

HPV54
No reference. Please see Genbank.

HPV55
No reference. Please see Genbank.

HPV56
Author: Delius, H.
Title: Direct Submission
Journal: Submitted (6 Aug. 1993) to the EMBL/GenBank/ DDBJ databases. H. Delius, Deutsches Krebsforschungszentrum, Abteilung ATV, Im Neuenheimer Feld 506, W 6900 Heidelberg, FRG
Author: Bergeron C, Barrasso R, Beaudenon S, Flamant P, Croissant O, Orth G
Title: Human papillomaviruses associated with cervical intraepithelial neoplasia. Great diversity and distinct distribution in low- and high-grade lesions
Journal: Am J Surg Pathol. 1992 July; 16(7):641-9.
Medline: 92411377

HPV57
Author: Hirsch-Behnam, A., Delius, H. and De Villiers, E. M.
Title: A comparative sequence analysis of two human papillomavirus (HPV) types 2a and 57
Journal: Virus Res. 18, 81-98 (1990)
Medline: 91188699
Author: de Villiers E M, Hirsch-Behnam A, von Knebel-Doeberitz C, Neumann C, zur Hausen H
Title: Two newly identified human papillomavirus types (HPV 40 and 57) isolated from mucosal lesions
Journal: Virology. 1989 July; 171(1):248-53.
Medline: 89299464

HPV59
Author: Rho, J., Roy-Burman, A., Kim, H., De Villiers, E. M., Matsukura, T. and Choe, J.
Title: Nucleotide sequence and phylogenetic classification of human papillomavirus type 59
Journal: Virology 203, 158-161 (1994)
Medline: 94303229

HPV61
Author: Matsukura T, Sugase M
Title: Identification of genital human papillomaviruses in cervical biopsy specimens: segregation of specific virus types in specific clinicopathologic lesions
Journal: Int J Cancer. 1995 Mar. 29; 61(1):13-22.
Medline: 95221020

HPV66
No reference. Please see Genbank.

HPV67
Author: Kirii, Y. and Matsukura, T.
Title: Nucleotide sequence and phylogenetic classification of human papillomavirus type 67
Journal: Virus Genes 17 (2), 117-121 (1998)
Medline: 99073695

HPV68
Author: Reuter, S., Delius, H., Kahn, T., Hofmann, B., Zur Hausen, H. and Schwarz, E.
Title: Characterization of a novel human papillomavirus DNA in the cervical carcinoma cell line ME180
Journal: J. Virol. 65, 5564-5568 (1991)
Medline: 91374616

HPV69
Author: Bernard, H.-U., Chan, S.-Y., Manos, M. M., Ong, C.-K., Villa, L. L., Delius, H., Peyton, C. L., Bauer, H. M., and Wheeler, C. M.
Title: Identification and assessment of known and novel human papillomaviruses by PCR amplification, restriction fragment length polymorphisms, nucleotide sequence, and phylogenetic algorithms
Journal: J. Infect. Dis. 170(5):1077-85 (1994)
Medline: 95052821

HPV70
Author: Forslund, O. and Hansson, B. G.
Title: Human papillomavirus type 70 genome cloned from overlapping PCR products: complete nucleotide sequence and genomic organization Journal: J. Clin. Microbiol. 34 (4), 802-809 (1996)
Medline: 96249586
HPV72
Author: Volter, C., He, Y., Delius, H., Roy-Burman, A., Greenspan, J. S., Greenspan, D. and de Villiers, E. M.
Title: Novel HPV types present in oral papillomatous lesions from patients with HIV infection
Journal: Int. J. Cancer 66 (4), 453-456 (1996)
Medline: 96213783
HPV5
Author: Zachow, K. R., Ostrow, R. S, and Faras, A. J.
Title: Nucleotide sequence and genome organization of human papillomavirus type 5
Journal: Virology 158, 251-254 (1987)
Medline: 87207670
Author: Ostrow, R. S., Zachow, K. R. and Faras, A. J.
Title: Molecular cloning and nucleotide sequence analysis of several naturally occurring HPV-5 deletion mutant genomes
Journal: Virology 158, 235-238 (1987)
Medline: 87207667
HPV8
Author: Fuchs, P. G., Iftner, T., Weninger, J. and Pfister, H.
Title: Epidermodysplasia verruciformis-associated human papillomavirus 8: Genomic sequence and comparative analysis
Journal: J. Virol. 58, 626-634 (1986)
Medline: 86200410
Author: Stubenrauch F, Malejczyk J, Fuchs P G, Pfister H
Title: Late promoter of human papillomavirus type 8 and its regulation
Journal: J Virol. 1992 June; 66(6):3485-93.
Medline: 92260618
Canine oral papillomavirus (COPV)
Author: Delius, H., Van Ranst, M. A., Jenson, B. A., Zur Hausen, H. and Sundberg, J. P.
Title: Canine oral papillomavirus genomic sequence: a unique 1.5-kb intervening sequence between the E2 and L2 open reading frames
Journal: Virology. 204(1):447-52 (1994)
Medline: 94378524
Rhesus papillomavirus type 1 (RHPV1)
Author: Ostrow, R. S., LaBresh, K. V. and Faras, A. J.
Title: Characterization of the complete RhPV 1 genomic sequence and an integration locus from a metastatic tumor
Journal: Virology 181 (1), 424-429 (1991)
Medline: 91135018
Author: Ostrow, R. S., Liu, Z., Schneider, J. F., McGlennen, R. C., Forslund, K. and Faras, A. J.
Title: The products of the E5, E6, or E7 open reading frames of RhPV 1 can individually transform NIH 3T3 cells or in cotransfections with activated ras can transform primary rodent epithelial cells
Journal: Virology 196 (2), 861-867 (1993)
Medline: 93383416
Cottontail rabbit papillomavirus (CRPV)
Author: Yaniv, M., Danos, O. and Giri, I.
Title: Genomic structure of the cottontail rabbit (Shope) papillomavirus
Journal: Proc. Natl. Acad. Sci. U.S.A. 82, 1580-1584 (1985)
Medline: 85166175
Rabbit oral papillomavirus (ROPV)
Author: O'Banion, M. K., Cialkowski, M. E., Reichmann, M. E. and Sundberg, J. P.
Title: Cloning and molecular characterization of an oral papillomavirus of domestic rabbits
Journal: Virology 162 (1), 221-231 (1988)
Medline: 88101370

---

We claim:

1. A method of producing a packaged DNA sequence comprising the steps of:
   (a) selecting a DNA sequence to be packaged and papillomaviral capsid sequences L1 and L2 wherein the DNA sequence is a full-length or near full-length papillomaviral genomic DNA sequence of at least 7 Kb,
   (b) co-transfecting the products of step (a) into transfectable cells, wherein the DNA sequence is packaged, and
   (c) purifying packaged particles.

2. The method of claim 1, wherein the DNA sequence is cloned into a plasmid, amplified in a suitable host, isolated and recircularized before step (b).

3. The method of claim 1 further comprising the step of modifying the capsid sequence by optimizing the codons and cloning the sequence into an expression plasmid.

4. The method of claim 1 wherein the cells are selected from the group consisting of 293T cells and 293T cell derivatives with additional SV40 T antigen overexpression.

5. The method of claim 1 wherein a native papillomaviral DNA genome is modified before packaging.

6. The method of claim 5 wherein the modification includes the insertion of a non-papillomaviral sequence into a segment of the papillomaviral genome.

7. The method of claim 1 wherein the papillomaviral capsid sequence is modified before packaging.

8. The method of claim 1 when the packaged particles are infectious.

* * * * *

SEQUENCE LISTING

```
<160> NUMBER OF SEQ ID NOS: 12

<210> SEQ ID NO 1
<211> LENGTH: 26
<212> TYPE: DNA
<213> ORGANISM: Artificial
<220> FEATURE:
<223> OTHER INFORMATION: Synthetic oligonucleotide

<400> SEQUENCE: 1
ttataaagtt gggtagccga tgcacg                                        26

<210> SEQ ID NO 2
<211> LENGTH: 24
<212> TYPE: DNA
<213> ORGANISM: Artificial
<220> FEATURE:
<223> OTHER INFORMATION: Synthetic oligonucleotide

<400> SEQUENCE: 2
tctacaactg ctaaacgcaa aaaa                                          24

<210> SEQ ID NO 3
<211> LENGTH: 24
<212> TYPE: DNA
<213> ORGANISM: Artificial
<220> FEATURE:
<223> OTHER INFORMATION: Synthetic oligonucleotide
```

```
<400> SEQUENCE: 3
ctggatattt gtacatctat ttgc                                              24

<210> SEQ ID NO 4
<211> LENGTH: 20
<212> TYPE: DNA
<213> ORGANISM: Artificial
<220> FEATURE:
<223> OTHER INFORMATION: Synthetic oligonucleotide

<400> SEQUENCE: 4
tctttatcag gttatattcc                                                   20

<210> SEQ ID NO 5
<211> LENGTH: 22
<212> TYPE: DNA
<213> ORGANISM: Artificial
<220> FEATURE:
<223> OTHER INFORMATION: Synthetic oligonucleotide

<400> SEQUENCE: 5
tttgcaacca gagacaactg at                                                22

<210> SEQ ID NO 6
<211> LENGTH: 22
<212> TYPE: DNA
<213> ORGANISM: Artificial
<220> FEATURE:
<223> OTHER INFORMATION: Synthetic oligonucleotide

<400> SEQUENCE: 6
agaggctgct gttatccaca at                                                22

<210> SEQ ID NO 7
<211> LENGTH: 22
<212> TYPE: DNA
<213> ORGANISM: Artificial
<220> FEATURE:
<223> OTHER INFORMATION: Synthetic oligonucleotide

<400> SEQUENCE: 7
aaatgacagc tcagaggagg ag                                                22

<210> SEQ ID NO 8
<211> LENGTH: 22
<212> TYPE: DNA
<213> ORGANISM: Artificial
<220> FEATURE:
<223> OTHER INFORMATION: Synthetic oligonucleotide

<400> SEQUENCE: 8
tgttaaatgc agtgaggatt gg                                                22

<210> SEQ ID NO 9
<211> LENGTH: 20
<212> TYPE: DNA
<213> ORGANISM: Artificial
<220> FEATURE:
<223> OTHER INFORMATION: Synthetic oligonucleotide

<400> SEQUENCE: 9
atgagcaatt acccgacagc                                                   20

<210> SEQ ID NO 10
```

```
<211> LENGTH: 20
<212> TYPE: DNA
<213> ORGANISM: Artificial
<220> FEATURE:
<223> OTHER INFORMATION: Synthetic oligonucleotide

<400> SEQUENCE: 10
gcacacaaaa gcaaagcaaa                                                    20

<210> SEQ ID NO 11
<211> LENGTH: 27
<212> TYPE: DNA
<213> ORGANISM: Artificial
<220> FEATURE:
<223> OTHER INFORMATION: Synthetic oligonucleotide

<400> SEQUENCE: 11
cccaaggcca accgcgagaa gatgacc                                            27

<210> SEQ ID NO 12
<211> LENGTH: 26
<212> TYPE: DNA
<213> ORGANISM: Artificial
<220> FEATURE:
<223> OTHER INFORMATION: Synthetic oligonucleotide

<400> SEQUENCE: 12
ccacatctgc tggaaggtgg acagcg                                             26
```